United States Patent
Fujita et al.

(10) Patent No.: US 6,485,799 B1
(45) Date of Patent: Nov. 26, 2002

(54) ANILINE DERIVATIVES, LIQUID-CRYSTAL COMPOSITION CONTAINING THE SAME, AND LIQUID-CRYSTAL DISPLAY ELEMENT

(75) Inventors: Atsuko Fujita, Chiba (JP); Norio Tamura, Chiba (JP); Hiroyuki Tekeuchi, Chiba (JP); Fusayuki Takeshita, Chiba (JP); Nobumasa Nakamura, Chiba (JP); Etsuo Nakagawa, Chiba (JP)

(73) Assignee: Chisso Corporation, Osaka (JP)

( * ) Notice: Subject to any disclaimer, the term of this patent is extended or adjusted under 35 U.S.C. 154(b) by 0 days.

(21) Appl. No.: 09/600,901

(22) PCT Filed: Nov. 22, 1999

(86) PCT No.: PCT/JP99/06505

§ 371 (c)(1),
(2), (4) Date: Jul. 24, 2000

(87) PCT Pub. No.: WO00/31019

PCT Pub. Date: Jun. 2, 2000

(30) Foreign Application Priority Data

Nov. 24, 1998 (JP) .......................................... 10-332609

(51) Int. Cl.$^7$ ......................... C09K 19/12; C09K 19/20; C09K 19/30; C09K 19/34; C07C 211/52; C07C 255/58; C07D 239/06

(52) U.S. Cl. ............... 428/1.1; 252/299.61; 252/299.63; 252/299.66; 252/299.67; 544/335; 558/411; 558/415; 558/425; 564/346; 564/366; 564/442; 570/127; 570/129; 570/141

(58) Field of Search ................. 252/299.61, 299.63, 252/299.66, 299.67; 428/1.1; 570/127, 129, 141; 544/335; 558/411, 415, 425; 564/346, 366, 442

(56) References Cited

U.S. PATENT DOCUMENTS 5,166,403 A 11/1992 Kurotaki et al.

FOREIGN PATENT DOCUMENTS

| JP | 10-88143 | 4/1998 |
| WO | 97/37960 | 10/1997 |
| WO | 98/16522 | 4/1998 |

OTHER PUBLICATIONS

CAPLUS 1994: 508067.*

* cited by examiner

Primary Examiner—Shean C. Wu
(74) Attorney, Agent, or Firm—Wenderoth, Lind & Ponack, L.L.P.

(57) ABSTRACT

A aniline derivative represented by general formula (1)

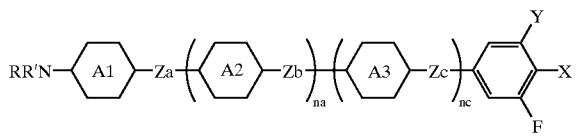

wherein R and R' represent independently each other alkyl with 1 to 10 carbon, alkoxyalkyl with 1 to 10 carbon, or hydrogen; x represents cyano, halogen, haloalkyl, haloalkyloxy, or 2-cyanoethynyl; Y represents fluorine or hydrogen; na and nc represent independently each other 0 or 1; Za, Zb, and Zc represent independently each other a single bond, 1,2-ethylene, carbonyloxy, or oxymethylene; ring A1 represents 1,4-phenylene in which hydrogen may be substituted by fluorine; ring A2 and ring A3 represent independently each other 1,4-cyclohexylene, 1,4-phenylene in which hydrogen may be substituted by fluorine, or 1,3-pyrimidine-2,5-diyl.

20 Claims, No Drawings

ANILINE DERIVATIVES, LIQUID-CRYSTAL COMPOSITION CONTAINING THE SAME, AND LIQUID-CRYSTAL DISPLAY ELEMENT

TECHNICAL FIELD

The present invention relates to a new liquid crystal compound, a liquid crystal composition containing the compound, and a liquid crystal display element using the composition.

BACKGROUND ART

A display element using characteristics such as optical anisotropy and dielectric anisotropy of liquid crystal materials has widely been utilized for a watch, an electric calculator and so on, and the display element utilizing a nematic phase is most common in practical. A display mode in this case includes a TN (twisted nematic) mode, a DS (dynamic scattering) mode, a GH (guest host) mode, a DAP (deformation of aligned phase) mode and so on. The liquid crystal materials require to exhibit a liquid crystal phase in a wide temperature range centering at room temperature, to be stable against water, light, heat, air, and so on, and in an electric field or in electromagnetic radiation under the condition used, and to have sufficient physical properties for driving a display element. The materials should be safe for the use of general consumers.

Values of physical properties such as optical anisotropy, dielectric anisotropy, and electric conductivity, which are required for the liquid crystal composition, depends on the display modes and shape of the elements.

It is required to have low viscosity, a wide temperature range, and a large value of dielectric anisotropy for the liquid crystal materials useful for a liquid crystal display element with the TN mode being widely used. However, no single compound which satisfies these conditions simultaneously has been known, and the liquid crystal materials used at present are composed by a mixture of liquid crystal compounds having their own characteristics.

Especially in recent, owing to the trend of thinning, lightning, and electric power-saving of a liquid crystal display panel, an important object for the development is to lower driving voltage of the panel. For lowering driving voltage of the panel, the shortest way is to develop liquid crystal materials having a large value of dielectric anisotropy which is possible to switch with a small quantity of electric power.

Development of some new compounds has been tried for the purpose of obtaining a compound with a large value of dielectric anisotropy. Ester compounds represented by formula (10) which are disclosed in Japanese Patent Publication Sho 60-55058 B (1985), compounds represented by formula (11) which are disclosed in Laid-Open Japanese Patent application Sho 63-502346 A (1988), or aniline derivatives represented by formula (12) which are disclosed in Z. Naturforsch., B; Anorg. Chem., Org. Chem 1979, 34B (8) 1092, are listed as an example of compounds having high dielectric anisotropy. These compounds do not seem to satisfy characteristics required for a liquid crystal compound such as a temperature range of liquid crystal phase, a value of optical anisotropy, viscosity, and a value of dielectric anisotropy.

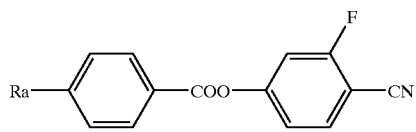

(10)

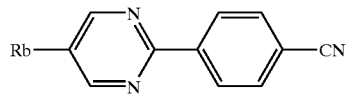

(11)

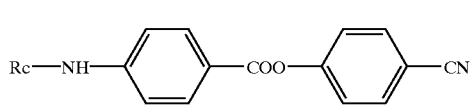

(12)

wherein Ra, Rb, and Rc represent alkyl.

An object of the present invention is to solve the defects in conventional technology described above, and is to provide a new liquid crystal compound having excellent properties as a liquid crystal component, namely a large value of dielectric anisotropy, a large value of optical anisotropy, a wide temperature range of a liquid crystal phase, and good miscibility with other liquid crystal materials, a liquid crystal composition containing the compound, and a liquid crystal display element composed from the composition.

THE PREFFERED EMBODIMENTS

To achieve the object described above, the present invention is characterized by the following components.

(1) An aniline derivative represented by general formula (1)

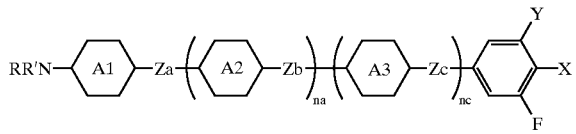

(1)

wherein R and R' represent independently each other alkyl with 1 to 10 carbon, alkoxyalkyl with 1 to 10 carbon, or hydrogen; X represents cyano, halogen, haloalkyl, haloalkyloxy, or 2-cyanoethynyl; Y represents fluorine or hydrogen; na and nc represent independently each other 0 or 1; Za, Zb, and Zc represent independently each other a single bond, 1,2-ethylene, carbonyloxy, or oxymethylene; ring A1 represents 1,4-phenylene in which hydrogen may be substituted by fluorine; ring A2 and ring A3 represent independently each other 1,4-cyclohexylene, 1,4-phenylene in which hydrogen may be substituted by fluorine, or 1,3-pyrimidine-2,5-diyl.

(2) The aniline derivative described in item (1) wherein both of na and nc is 0.

(3) The aniline derivative described in item (2) wherein X is halogen, trihaloalkyl, or trihaloalkyloxy.

(4) The aniline derivative described in item (2) wherein X is cyano or 2-cyanoethynyl.

(5) The aniline derivative described in item (2) wherein Za is carbonyloxy.

(6) The aniline derivative described in item (5) wherein X is cyano or 2-cyanoethynyl.

(7) The aniline derivative described in item (1) wherein na is 1, nc is 0.

(8) The aniline derivative described in item (7) wherein x is halogen.

(9) The aniline derivative described in item (7) wherein X is cyano or 2-cyanoethynyl.

(10) The aniline derivative described in item (7) wherein Zb is carbonyloxy.

(11) The aniline derivative described in item (9) wherein Zb is carbonyloxy.

(12) The aniline derivative described in item (1) wherein both of na and nc is 1.

(13) A liquid crystal composition containing one or more aniline derivatives described in any one of items (1) to (12).

(14) The liquid crystal composition characterized in that the composition comprises one or more compounds described in any one of items (1) to (12) as the first component, and one or more compounds selected from the group consisting of general formulae (2), (3), and (4).

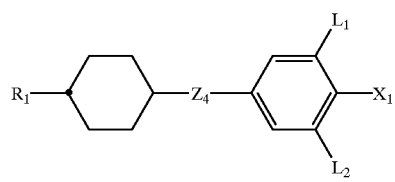

(2)

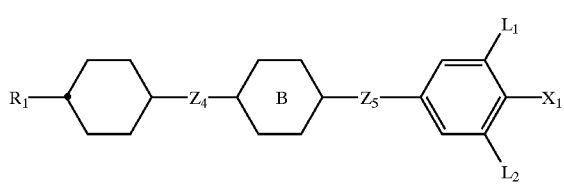

(3)

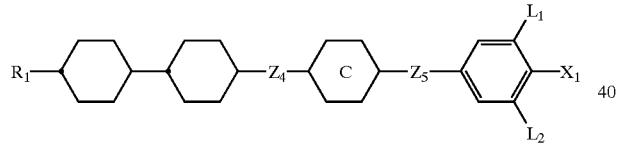

(4)

wherein $R_1$ represents alkyl having 1 to 10 carbon, any methylene nonadjacent each other in the alkyl may be replaced with oxygen or —CH=CH—, and any hydrogen in the alkyl may be replaced with fluorine; $X_1$ represents fluorine, chlorine, —OCF$_3$, —OCF$_2$H, —CF$_3$, —CF$_2$H, —CFH$_2$, —OCF$_2$CF$_2$H, or —OCF$_2$CFHCF$_3$; $L_1$ and $L_2$ independently each other represent hydrogen or fluorine; $Z_4$ and $Z_5$ independently each other 1,2-ethylene, 1,4-butylene, —COO—, —CF$_2$O—, —OCF$_2$—, —CH=CH—, or a single bond; a ring B represents trans-1,4-cyclohexylene, 1,3-dioxane-2,5-diyl, or 1,4-phenylene in which hydrogen on the ring may be substituted by fluorine; a ring C represents trans-1,4-cyclohexylene or 1,4-phenylene in which hydrogen on the ring may be substituted by fluorine.

(15) The liquid crystal composition characterized in that the composition comprises one or more compounds described in any one of items (1) to (12) as the first component and one or more compounds selected from the group represented in general formulae (5) and (6) as the second component.

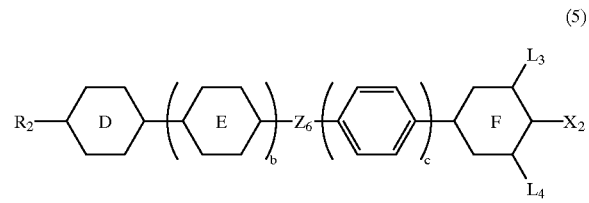

(5)

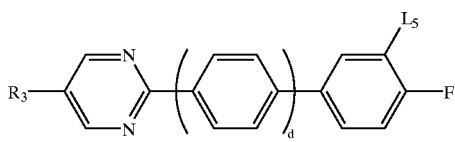

(6)

wherein $R_2$ and $R_3$ represent alkyl having 1 to 10 carbon and any methylene nonadjacent each other in the alkyl may be replaced with oxygen or —CH=CH—, and any hydrogen in the alkyl may be replaced with fluorine; $X_2$ represents —CN or —C≡C—CN; a ring D represents trans-1,4-cyclohexylene, 1,4-phenylene, or pyrimidine-2,5-diyl; a ring F represents trans-1,4-cyclohexylene or 1,4-phenylene; $Z_6$ represent 1,2-ethylene, —COO— or a single bond; $L_3$, $L_4$, and $L_5$ represent hydrogen or fluorine; b, c, and d represent independently each other 0 or 1.

(16) The liquid crystal composition characterized in that the composition comprises one or more compounds described in any one of items (1) to (12) as the first component, one or more compounds selected from the group represented in general formulae (2), (3), and (4) as the second component, and one or more compounds selected from the group represented in general formulae (7), (8), and (9) as the third component.

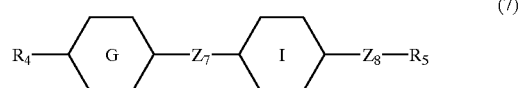

(7)

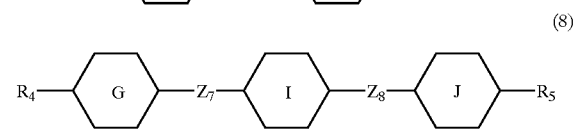

(8)

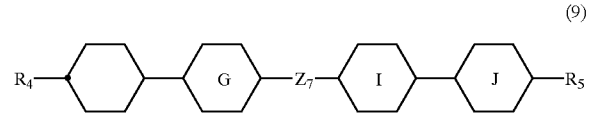

(9)

wherein $R_4$ and $R_5$ represent alkyl having 1 to 10 carbon, and any methylene nonadjacent each other in the alkyl may be replaced with oxygen or —CH=CH—, and any hydrogen in the alkyl may be replaced with fluorine; rings G, I, and J represent each independently trans-1,4-cyclohexylene, pyrimidine-2,5-diyl, and 1,4-phenylene in which hydrogen in the ring may be substituted with fluorine; $Z_7$ and $Z_8$ each independently represent —C≡C—, —COO—, —CH2CH2—, —CH=CH— or a single bond.

(17) The liquid crystal composition characterized in that the composition comprises one or more compounds described in any one of items (1) to (12) as the first component, one or more compounds selected from the group represented in general formulae (5) and (6) as the second component, and one or more compounds selected from the group represented in general formulae (7), (8), and (9) as the third component.

(18) The liquid crystal composition characterized in that the composition comprises one or more compounds described in any one of items (1) to (12) as the first component, one or more compounds selected from the group represented in general formulae (2), (3), and (4) as the second component, and one or more compounds selected from the group represented in general formulae (5) and (6) as the third component.

(19) The liquid crystal composition characterized in that the composition further comprises one or more optically active compounds in addition to the liquid crystal composition described in any one of items (13) to (18).

(20) A liquid crystal display element composed by the use of the liquid crystal composition described in any one of items (13) to (19).

BEST EMBODIMENTS OF THE INVENTION

The liquid crystal compound of the present invention has a very large value of dielectric anisotropy compared with other liquid crystal molecules having similar molecular weight, and has a wide temperature range of a liquid crystal phase compared with a similar compound, and further is new and excellent in miscibility with another liquid crystal compounds.

The liquid crystal compound of the present invention is characterized in that it has alkylamino in one terminal of the molecule and has a benzene ring substituted with fluorine at the 3-position in the another terminal. By the introduction of fluorine in the position, the very high dielectric anisotropy was realized in the compound of the present invention, compared with the known compounds. Namely, the compound of the present invention has a large value of dielectric anisotropy which can not be explained by simple sum of dielectric anisotropy exhibited by a similar compound without fluorine-substituent which is known to an expert and dielectric anisotropy attained by electron-withdrawing character of fluorine.

One or two is preferable for the number of fluorine on the benzene ring in the terminal and the position of the substitution is preferable for the next of an electron-withdrawing group in long altitude direction of the molecule. The compound with two fluorine has a larger value of dielectric anisotropy than that with one fluorine, and the compound with one fluorine has a wide temperature range of a liquid crystal phase. The compound of the present invention with fluorine on another benzene ring in the molecule shows especially large value of dielectric anisotropy and is important, and the position of the substitution is preferable being close to an electron-withdrawing group in the direction of molecular axis.

Typical compound is shown in formulae (1-1) to (1-9) among the compounds of the present invention represented by general formula (1).

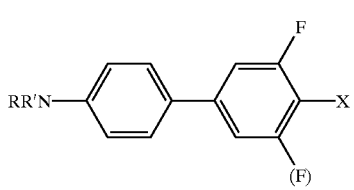
(1-1)

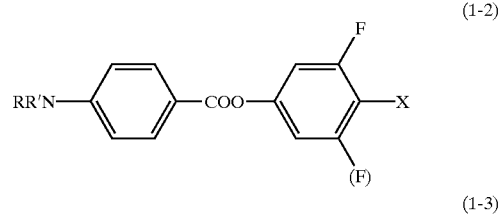
(1-2)

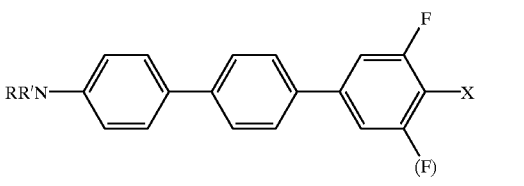
(1-3)

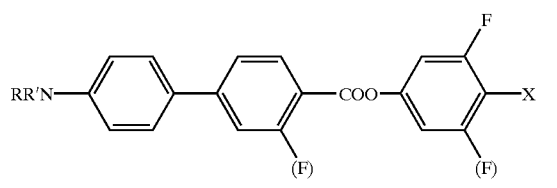
(1-4)

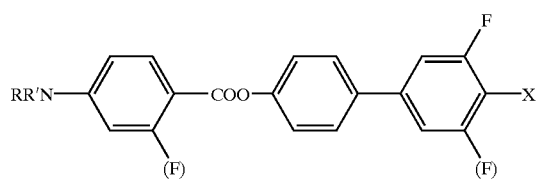
(1-5)

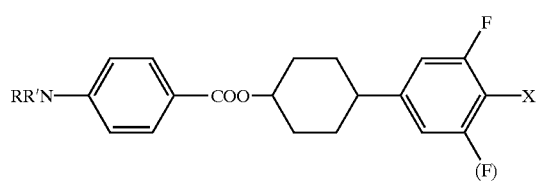
(1-6)

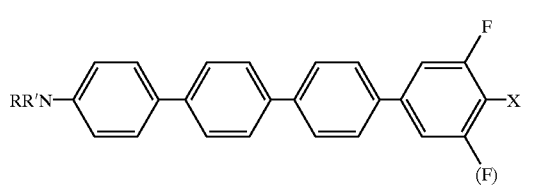
(1-7)

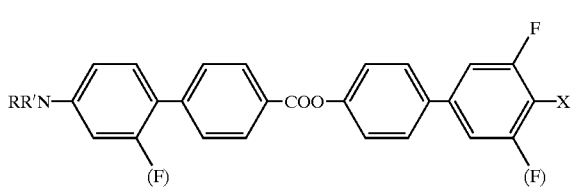
(1-8)

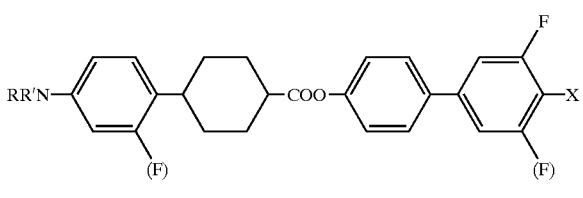
(1-9)

wherein $R_1$, $R_2$, and X represent the same with the meaning described above.

Among these, the compound of the present invention having highly conjugated structure represented by formulae (1-1), (1-3), and (1-7) has both a large value of dielectric anisotropy and a large value of optical anisotropy, and is an important liquid crystal material. The ester derivative presented by (1-2), (1-4), (1-5), (1-6), (1-8), and (1-9) has especially a large value of dielectric anisotropy, a wide temperature range of a liquid crystal phase, and a large value of optical anisotropy, and is important. The compound of the present invention having a cyclohexane ring, which is represented by formulae (1-6) and (1-9), has a large value of dielectric anisotropy and good miscibility, and a wide temperature range of a liquid crystal phase, and is important.

The liquid crystal composition of the present invention contains preferably one or more compounds represented by general formula (1) in 0.1 to 99.9% by weight to exhibit excellent characteristics.

More preferably the liquid crystal composition of the present invention is completed by mixing a compound selected from compounds represented by general formulae (2) to (9) according to the purpose of the liquid crystal composition, to the first component containing one or more compounds represented by general formula (1).

A preferable example of the compound represented by general formula (2) which is used for the liquid crystal composition of the present invention is the compound of formulae (2-1) to (2-9), a preferable example of the compound presented by general formula (3) is the compound of general formulae (3-1) to (3-69), and a preferable example of the compound represented by general formula (4) is the compound of general formulae (4-1) to (4-24), respectively.

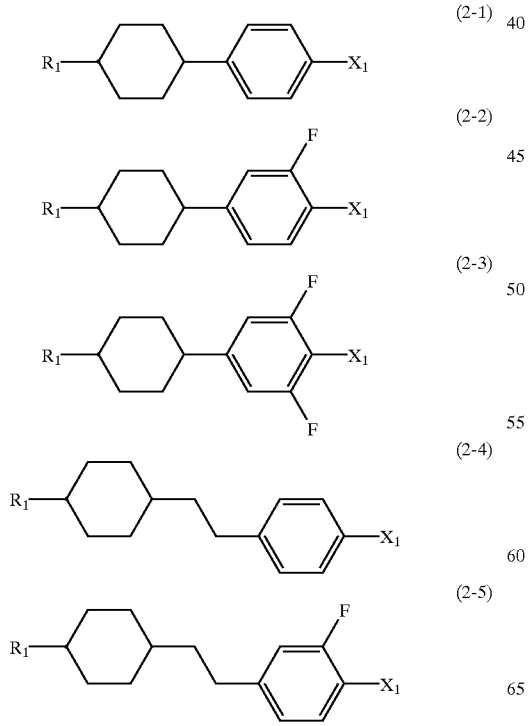
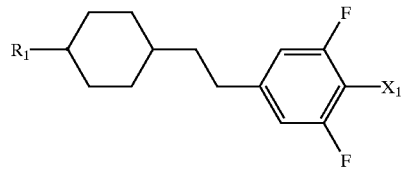
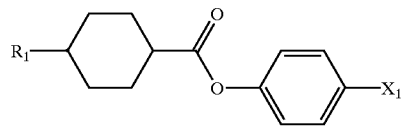
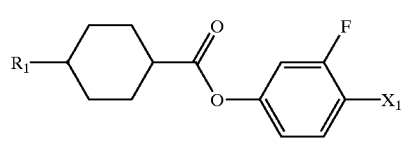
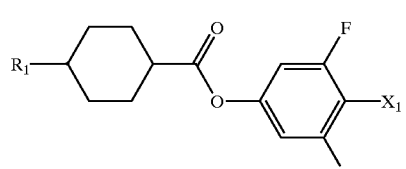
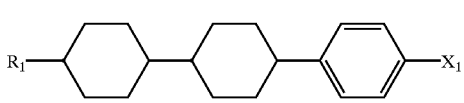
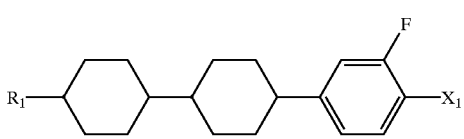
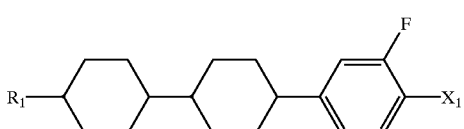
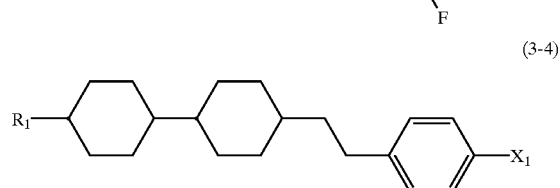
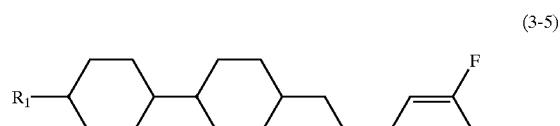
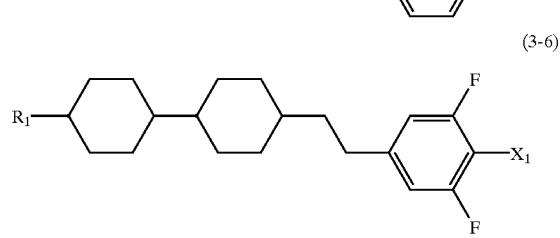

-continued
(3-7)
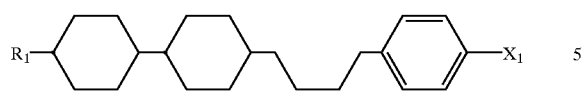
(3-8)
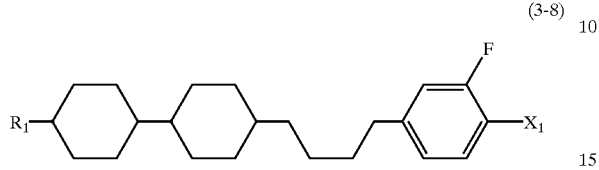
(3-9)
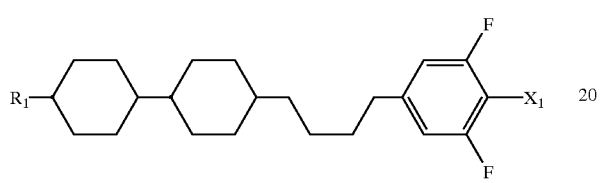
(3-10)
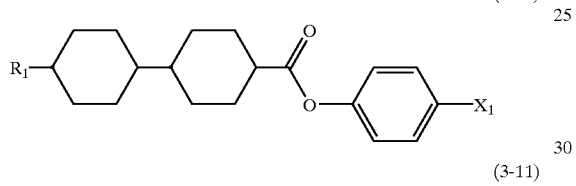
(3-11)
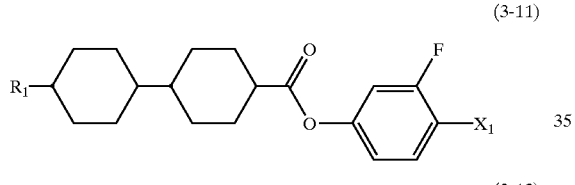
(3-12)
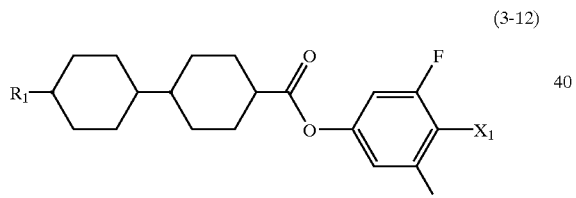
(3-13)
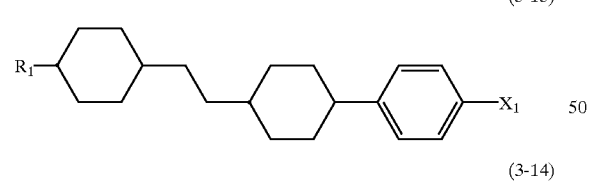
(3-14)
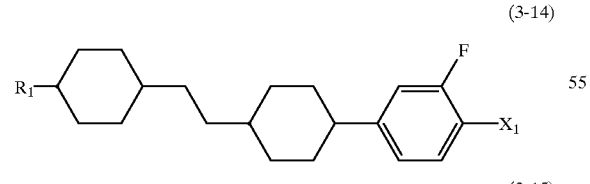
(3-15)
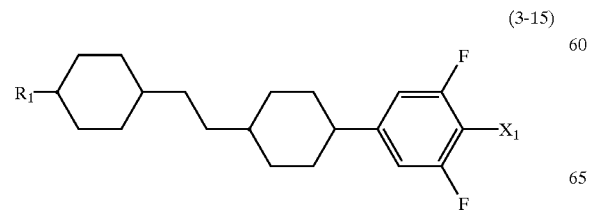
-continued
(3-16)
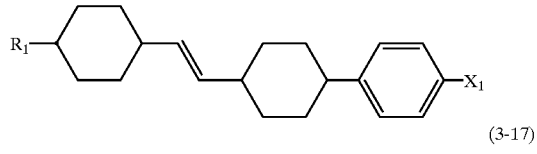
(3-17)
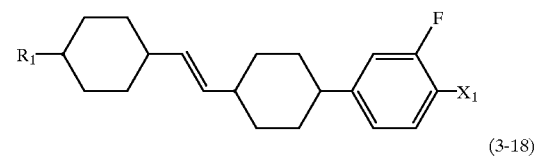
(3-18)
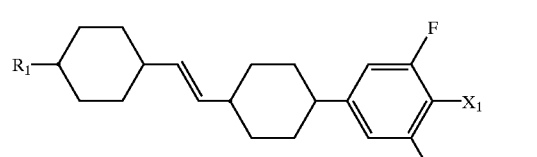
(3-19)
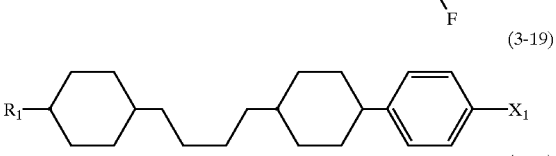
(3-20)
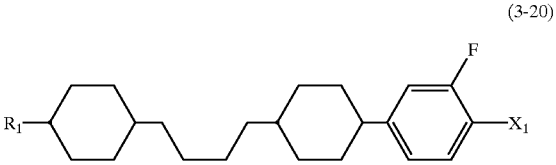
(3-21)
(3-22)
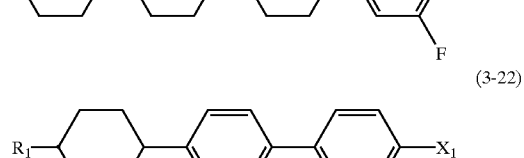
(3-23)
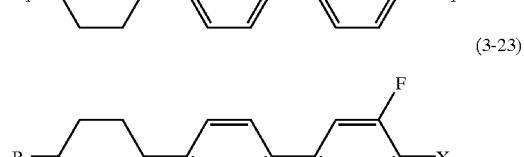
(3-24)
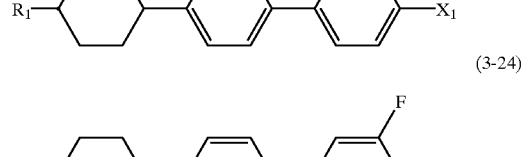
(3-25)
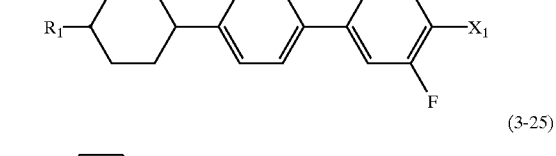

(3-26) 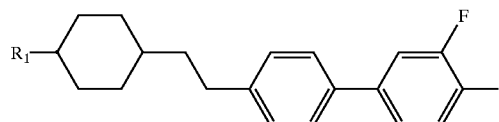
(3-27) 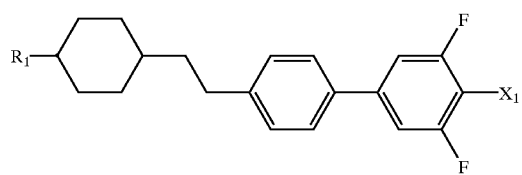
(3-28) 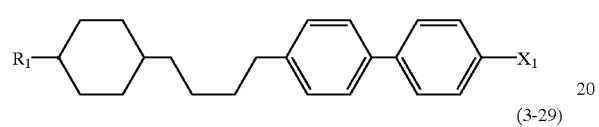
(3-29) 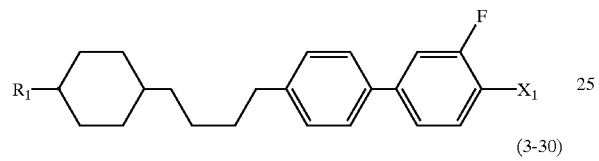
(3-30) 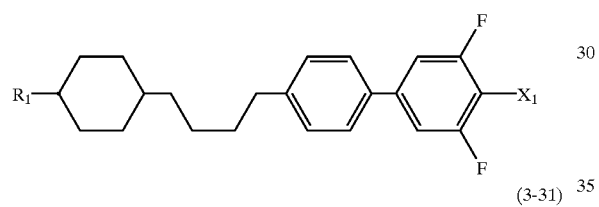
(3-31) 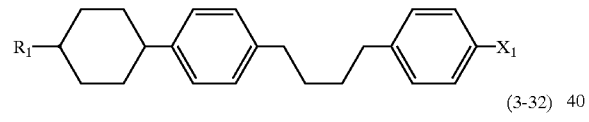
(3-32) 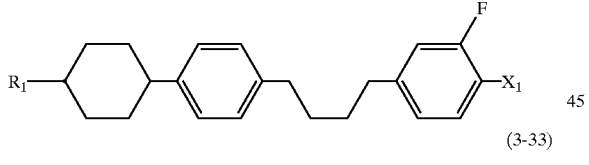
(3-33) 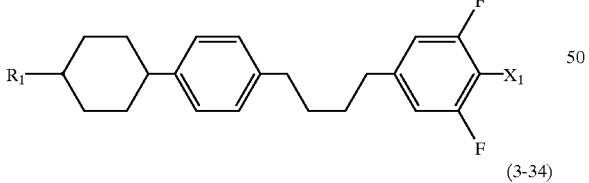
(3-34) 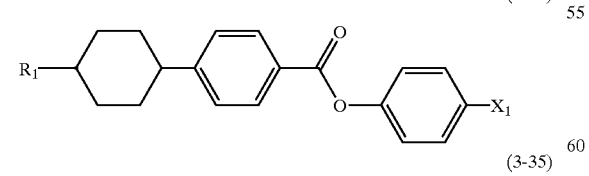
(3-35) 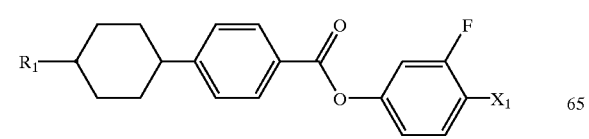
(3-36) 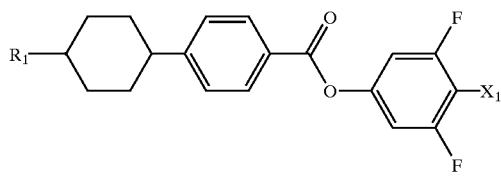
(3-37) 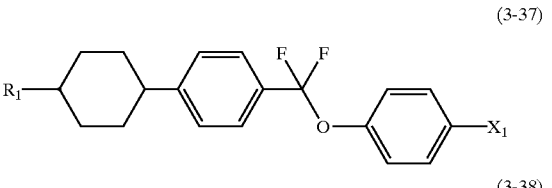
(3-38) 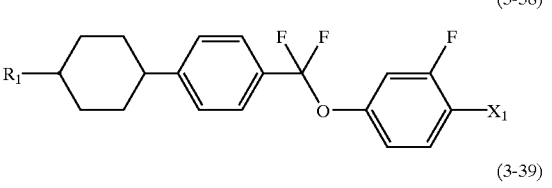
(3-39) 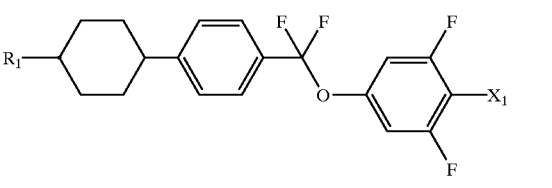
(3-40) 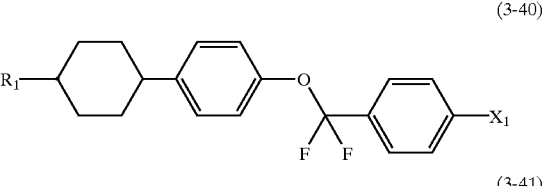
(3-41) 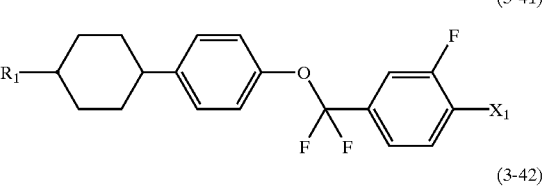
(3-42) 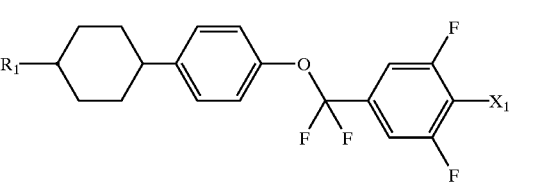
(3-43) 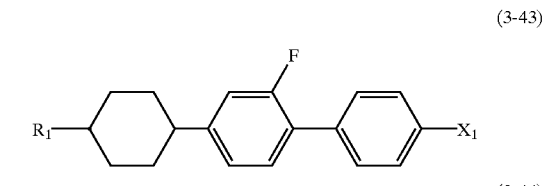
(3-44) 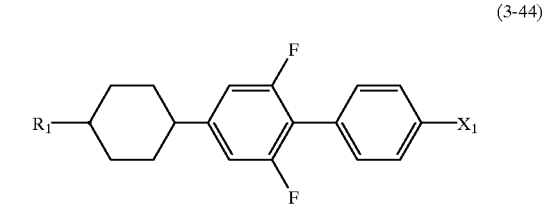

(3-45)
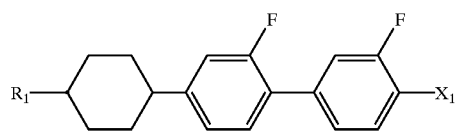
(3-46)
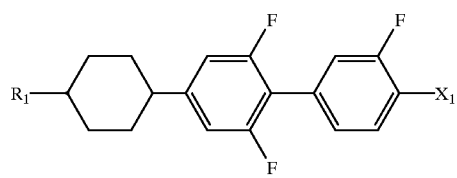
(3-47)
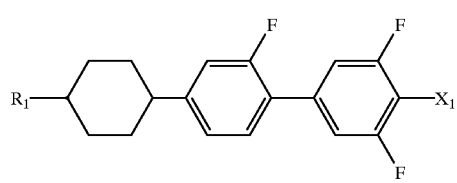
(3-48)
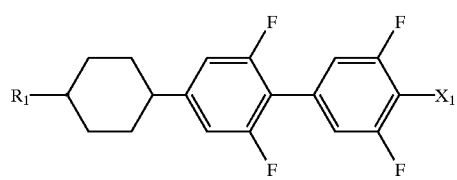
(3-49)
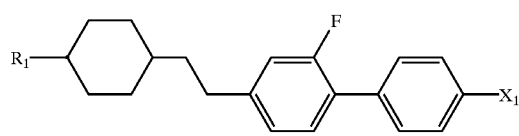
(3-50)
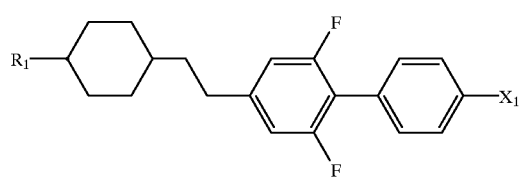
(3-51)
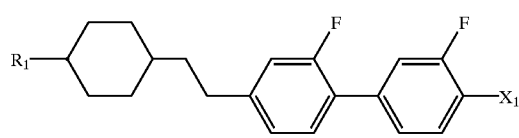
(3-52)
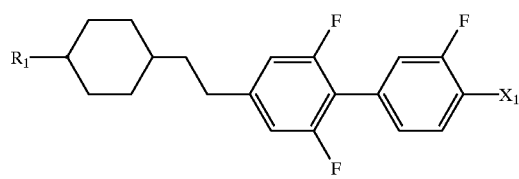
(3-53)
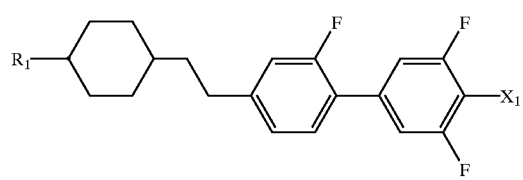
(3-54)
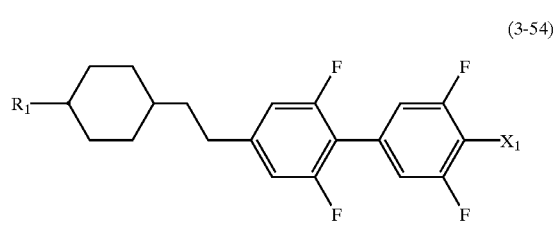
(3-55)
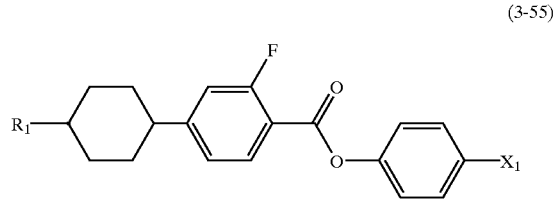
(3-56)
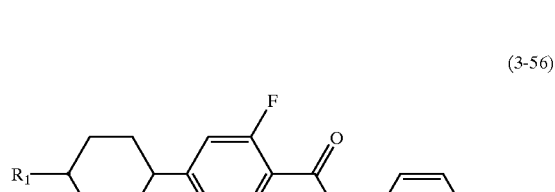
(3-57)
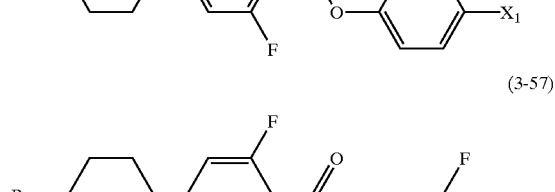
(3-58)
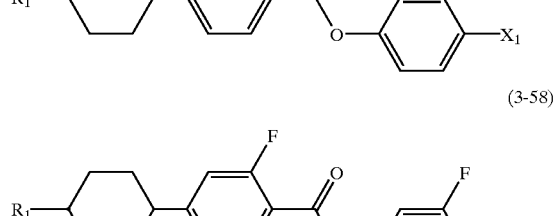
(3-59)
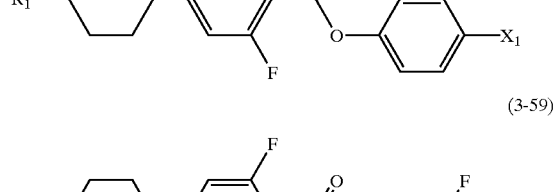
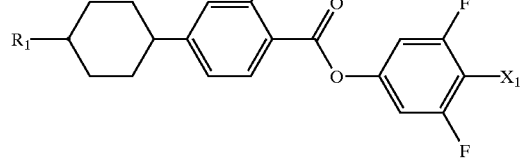

(3-60)
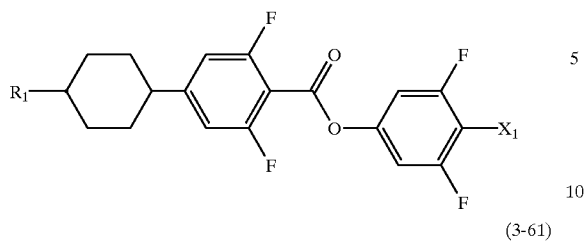
(3-61)
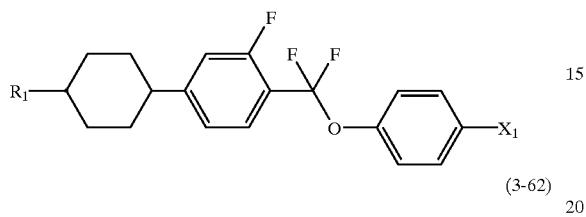
(3-62)
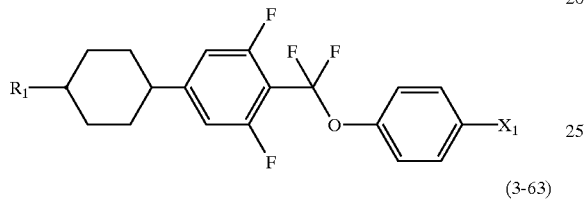
(3-63)
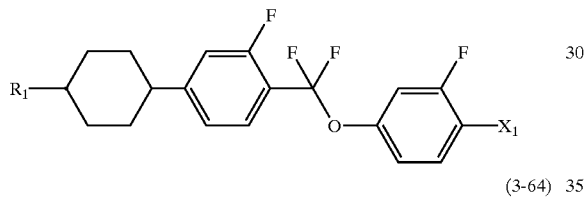
(3-64)
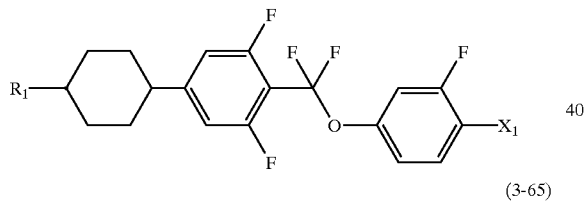
(3-65)
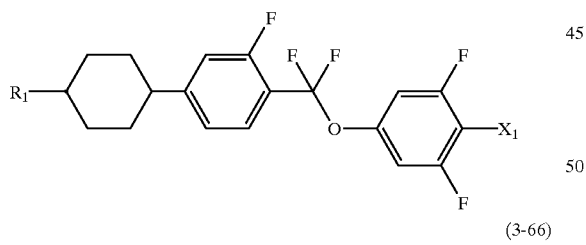
(3-66)
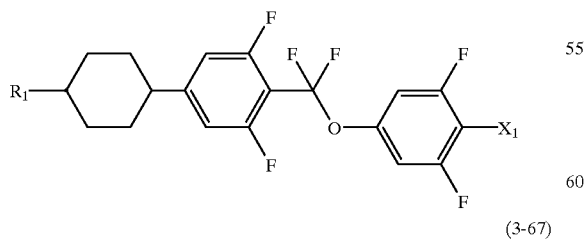
(3-67)
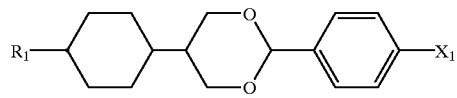
(3-68)
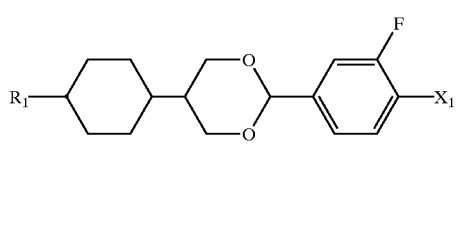
(3-69)
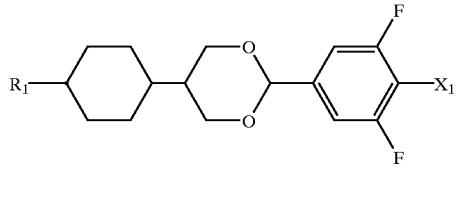
(4-1)
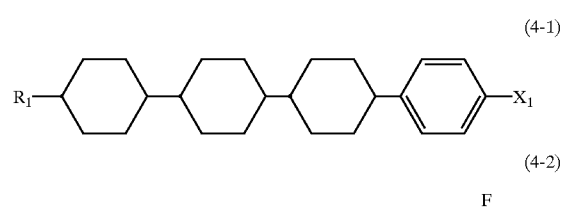
(4-2)
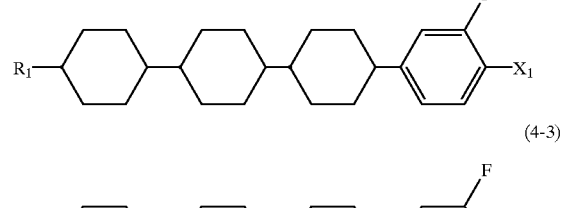
(4-3)
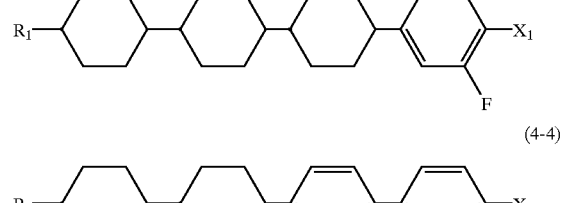
(4-4)
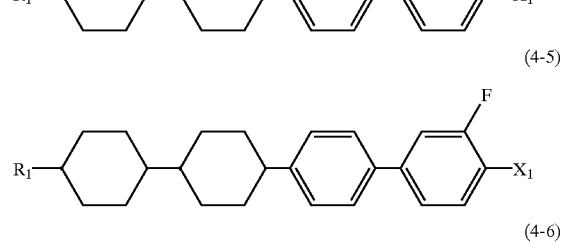
(4-5)
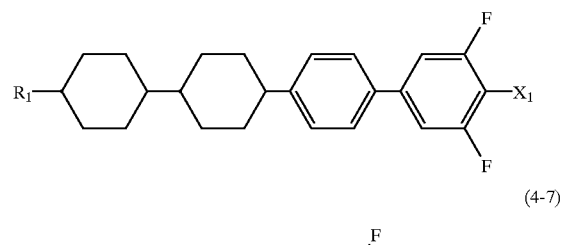
(4-6)
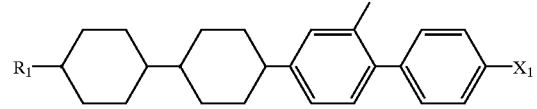
(4-7)

-continued
(4-8)
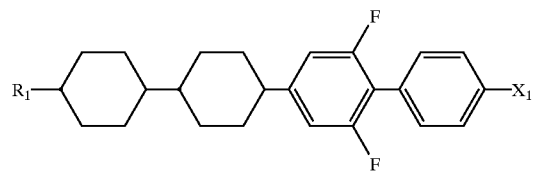
(4-9)
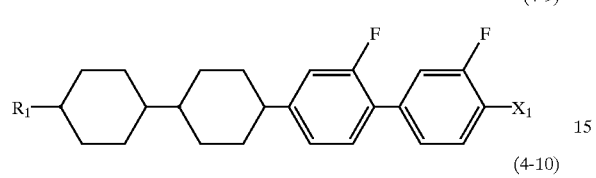
(4-10)
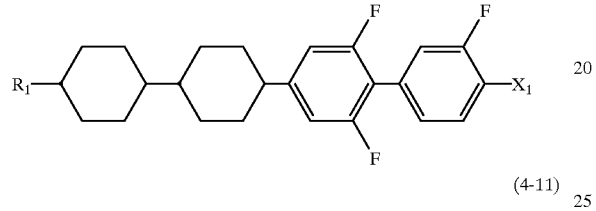
(4-11)
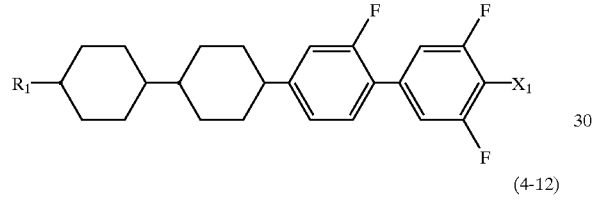
(4-12)
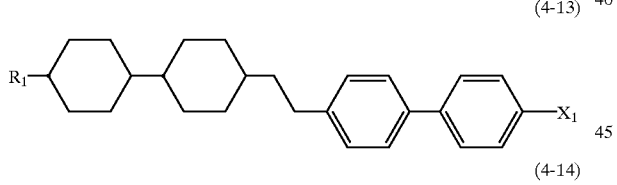
(4-13)
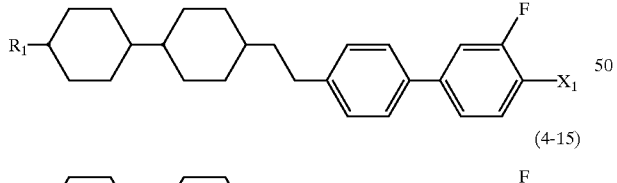
(4-14)
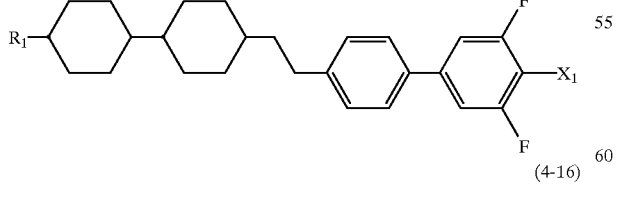
(4-15)
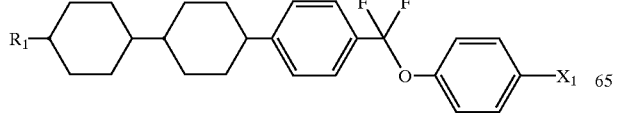
(4-16)
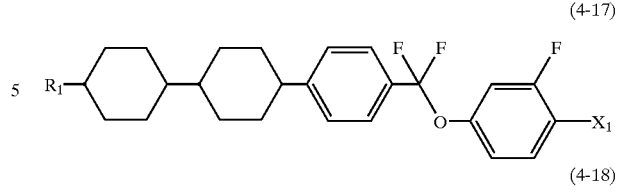
-continued
(4-17)
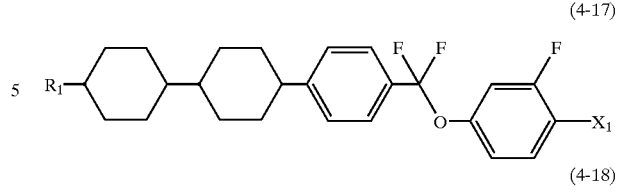
(4-18)
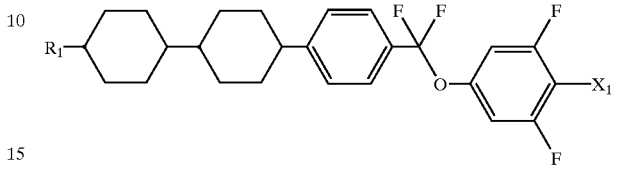
(4-19)
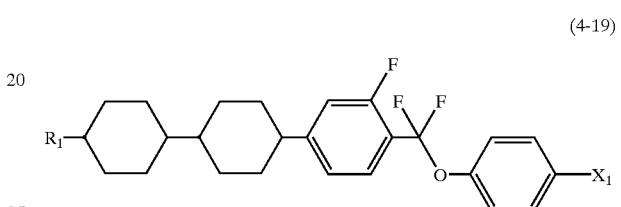
(4-20)
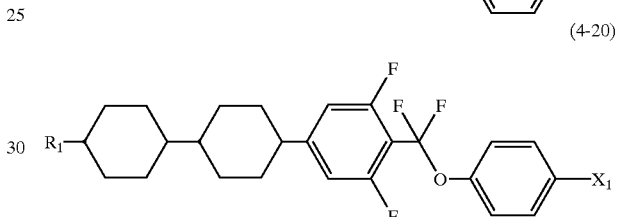
(4-21)
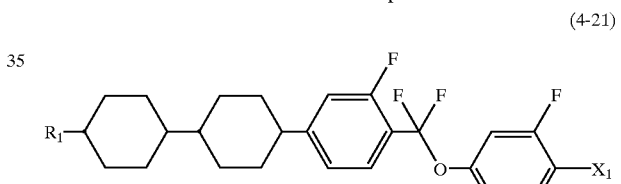
(4-22)
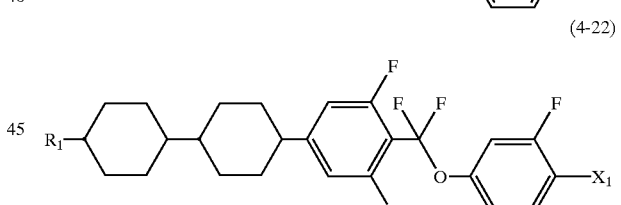
(4-23)
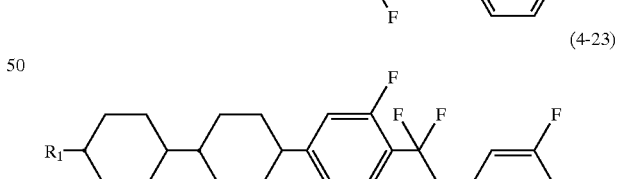
(4-24)
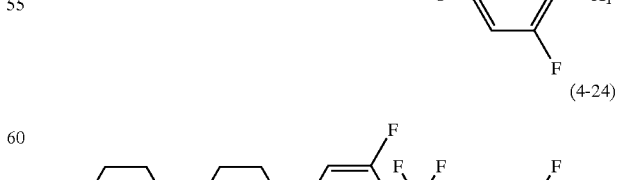

wherein $R_1$ and $X_1$ represent the same with the meaning described above.

The compound represented by general formulae (2) to (4) has a positive value of dielectric anisotropy and is quite excellent in thermal stability and in chemical stability. In the preparation of a liquid crystal composition for the TN mode, an amount of the compound represented by general formulae (2) to (4) is in the range of 1 to 99% by weight based on total weight of the liquid crystal composition, preferably 10 to 97% by weight, more preferably 40 to 95% by weight.

Preferable examples of the compound represented by general formula (5) used for the liquid crystal composition of the present invention are the compound of formulae (5-1) to (5-40) and preferable examples of the compound represented by general formula (6) are the compounds of formulae (6-1) to (6-3).

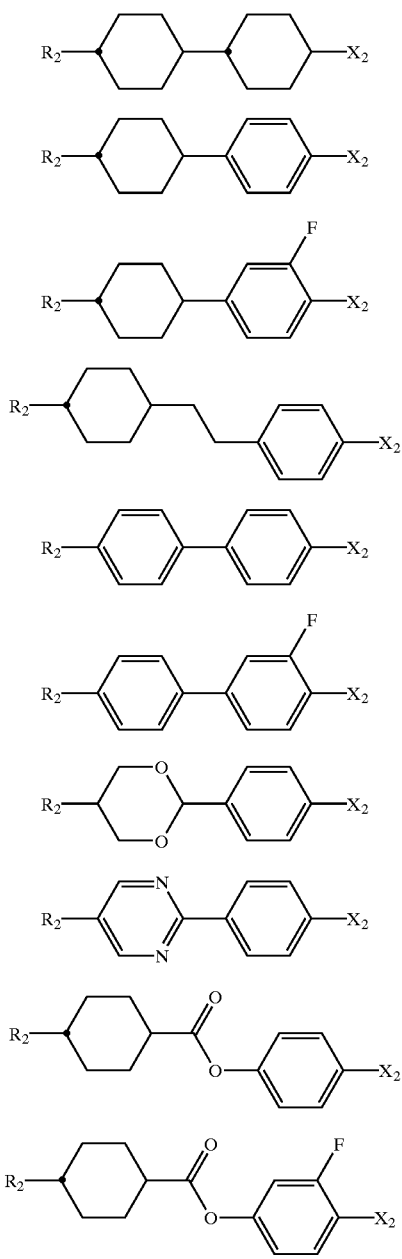

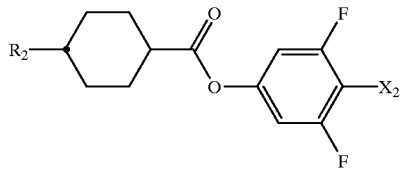

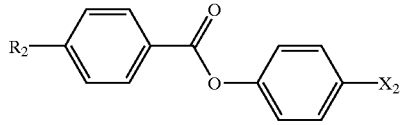

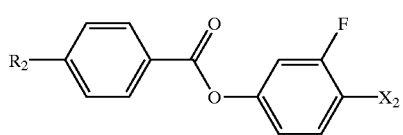

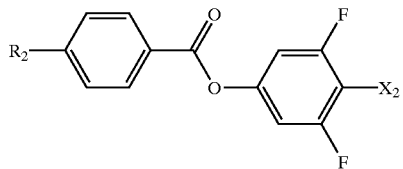

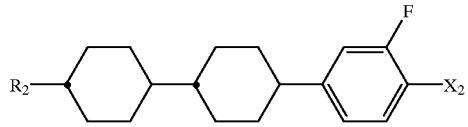

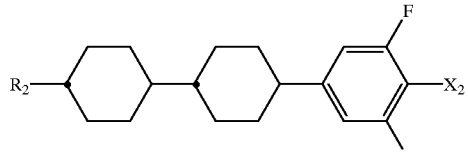

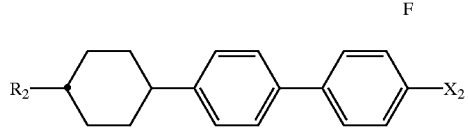

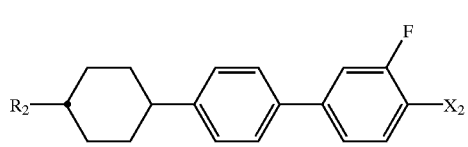

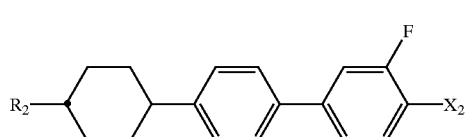

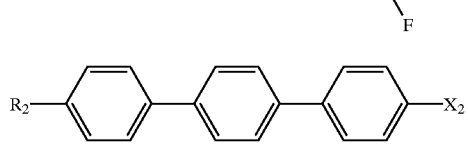

-continued (5-22)

(5-23)

(5-24)

(5-25)

(5-26)

(5-27)

(5-28)

(5-29)

(5-30)

(5-31)

-continued (5-32)

(5-33)

(5-34)

(5-35)

(5-36)

(5-37)

(5-38)

(5-39)

(5-40)

(6-1)

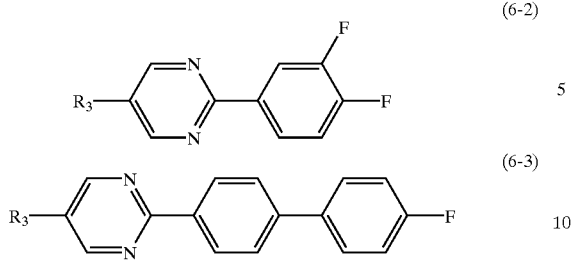

wherein $R_2$, $R_3$ and $X_2$ represent the same with the meaning described above.

The compound represented by general formulae (5) and (6) has a large value of dielectric anisotropy and is added to the liquid crystal composition for the purpose of lowering the threshold voltage of the composition. The compound is also used for the purpose such as adjusting viscosity, adjusting a value of optical anisotropy, and widening a temperature range of a liquid crystal phase of the liquid crystal composition, and for the purpose of improving the steepness of the threshold voltage characteristics Preferable examples of the compound represented by general formula used for the liquid crystal composition of the present invention are the compound of formulae (7-1) to (7-11), preferable examples of the compound represented by general formula (8) are the compound of formulae (8-1) to (8-18), and preferable examples of the compounds represented by general formula (9) are the compound of formulae (9-1) to (9-6).

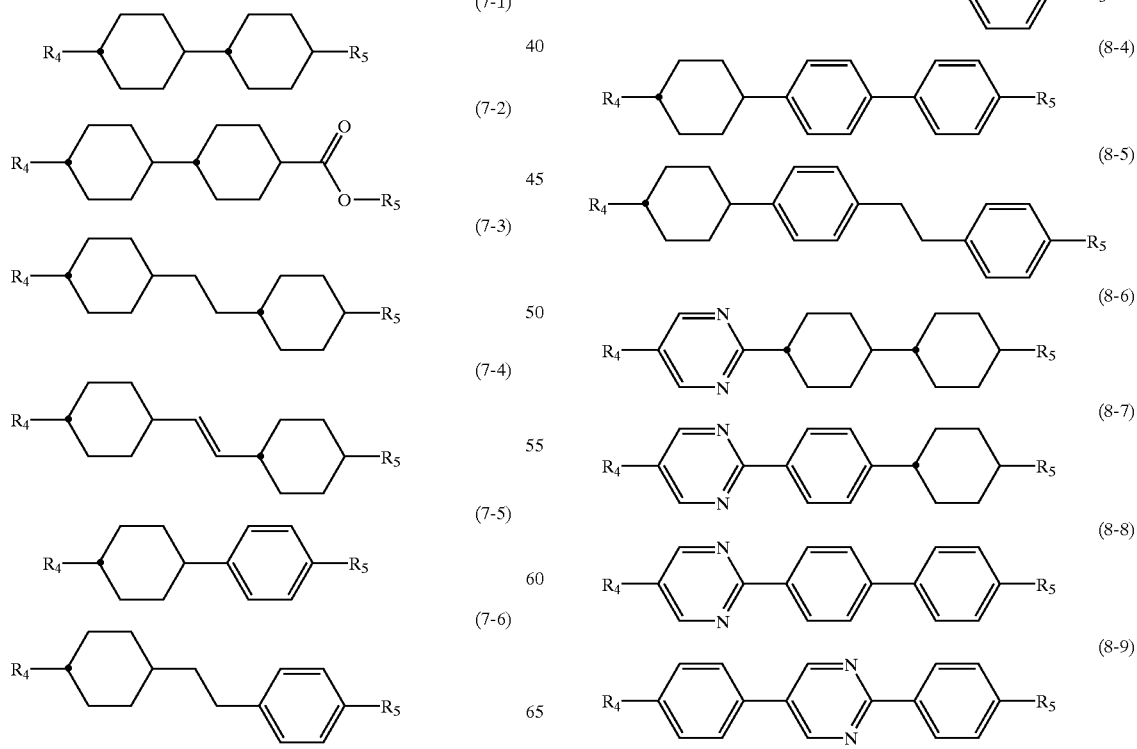

(8-10)
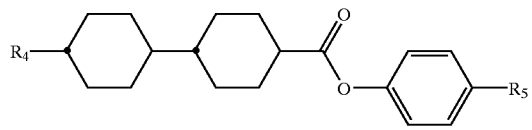

(8-11)
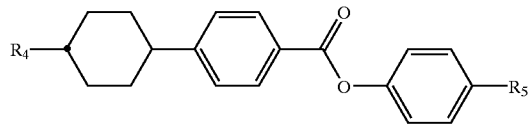

(8-12)
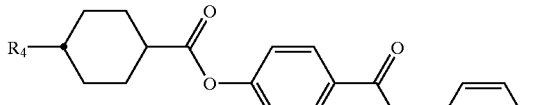

(8-13)
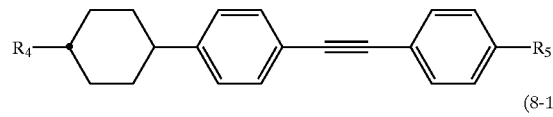

(8-14)
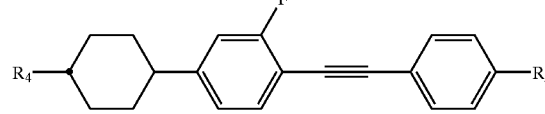

(8-15)
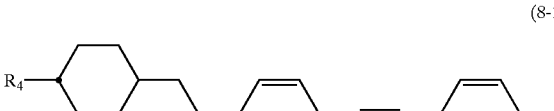

(8-16)
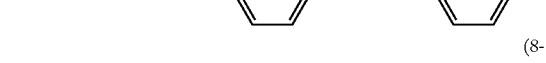

(8-17)
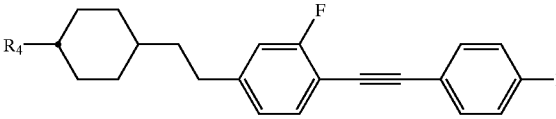

(8-18)
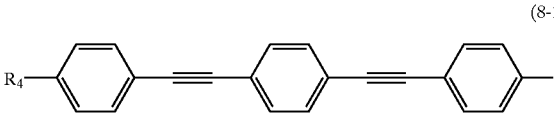

(9-1)
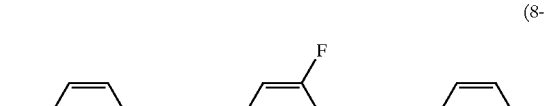

(9-2)
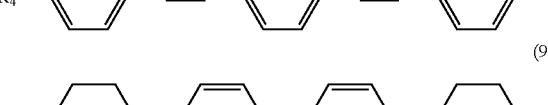

(9-3)
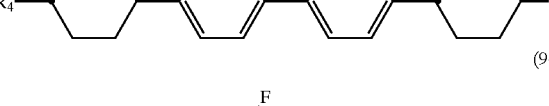

(9-4)
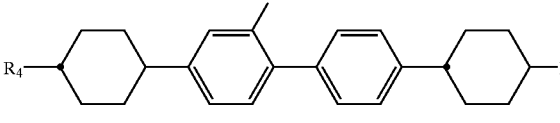

(9-5)
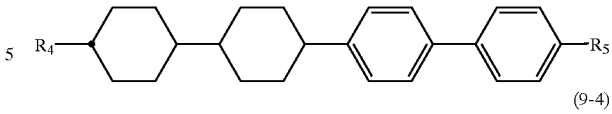

(9-6)
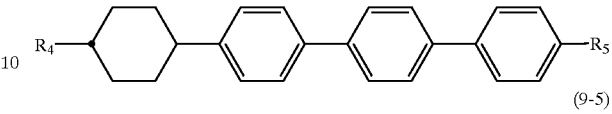

wherein $R_4$, $R_5$, $R_6$, $R_7$, and $R_8$ represents the same with the meaning described above.

The compound represented by general formula (7), (8), and (9) has negative or small positive value of dielectric anisotropy. The compound represented by general formula (7) and (8) is used mainly for the purpose of lowering viscosity of the liquid crystal composition, and/or of adjusting a value of optical anisotropy. The compound represented by general formula (9) is used for the purpose of widening a temperature range of nematic phase by increasing the clearing point of the liquid crystal composition and/or of adjusting a value of optical anisotropy.

The compound represented by general formulae (5) to (9) is useful in the preparation of the liquid crystal composition especially for the STN mode and the TN mode.

In the preparation of liquid crystal composition for the TN mode and the STN mode, the compound represented by general formulae (5) to (9) is used in the range of 1 to 99% by weight based on total weight of the liquid crystal composition, preferably 10 50 97% by weight, more preferably 40 to 95% by weight. The compound of (2) to (4) may partly be used for the composition.

The liquid crystal composition of the present invention is prepared by conventional methods. In general, the method is to dissolve each component at high temperature. Another method is removal of solvent under reduced pressure after each component was mixed and dissolved in the solvent which dissolve the liquid crystals.

The liquid crystal composition of the present invention is improved and optimized according to the intended use by the action of proper additives. Such additives are known to a person skilled in the art, and are described in the literature in detail.

Optically active compounds are generally added for the purpose of inducing helical structure of liquid crystals, adjusting a twist angle required, and avoiding a reverse twist in the liquid crystal composition for the STN mode and the TFT type. Known optically active compounds can be added to the liquid crystal composition of the present invention for such purpose. Preferable examples of the optically active compound are the following compound (C-1) to (C-8).

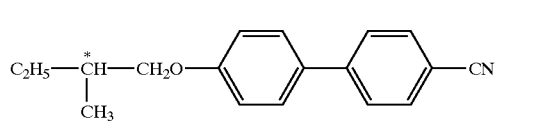 (C-1)

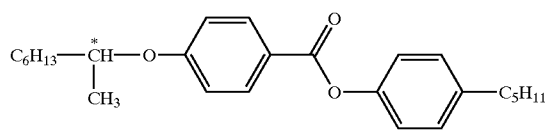 (C-2)

(C-3)

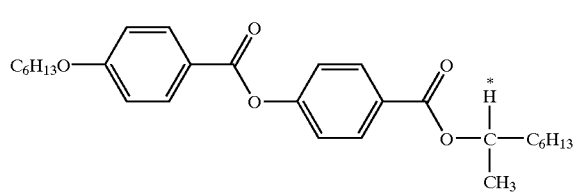

(C-4)

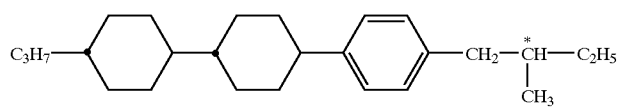

(C-5)

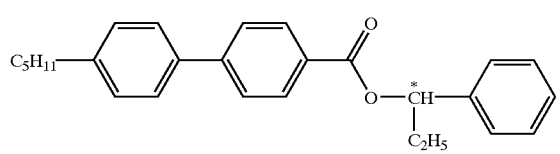

(C-6)

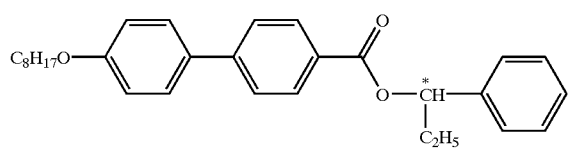

(C-7)

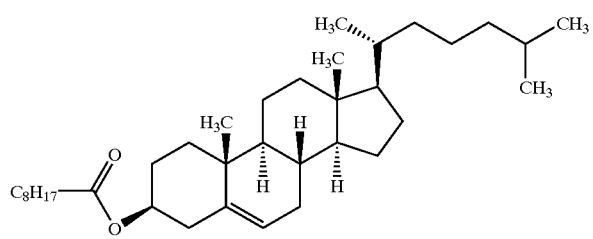

(C-8)

The liquid crystal composition can be used for the guest-host (GH) mode by adding a dichroic dye such as a merocyanine type, a styryl type, an azo type, an azomethine type, an azoxy type, a quinophthalone type, an anthraquinone type, and a tetrazine type. Alternatively, the liquid crystal composition can be used as NCAP which is prepared by the microencapsulation of nematic liquid crystals, or as a polymer dispersed liquid crystal display element (PDLCD) represented by a polymer net work liquid crystal display element (PNLCD) prepared by forming a polymer of three-dimensional reticulated structure in liquid crystals. Further the liquid crystal composition can be used for an electrically controlled birefringence (ECB) mode or a dynamic scattering (DS) mode.

Examples of the liquid crystal composition of the present invention are in the following. The compound in the examples is represented by using symbols defined in Table 1. Physical properties are represented by the following symbols. A clearing point is NI (° C.), viscosity at 20° C. is η (mPa·s), a value of optical anisotropy is Δn, a value of dielectric anisotropy is Δε, threshold voltage measured at a liquid crystal cell having cell thickness of 9.1 μm is Vth (V)

TABLE 1

| Method for designating compounds by using symbols<br>R—(A$_1$)—Z$_1$— . . . —Z$_n$—(A$_n$)—X | |
|---|---|
| 1) Left side terminal group R— | Symbol |
| C$_n$H$_{2n+1}$— | n— |
| C$_n$H$_{2n+1}$O— | nO— |
| C$_n$H$_{2n+1}$OC$_m$H$_{2m}$— | nOm— |
| C$_n$H$_{2n+1}$N— | nN— |
| C$_n$H$_{2n+1}$N(CH$_3$)— | nN(1)— |
| CH$_2$=CH— | V— |
| CH$_2$=CHC$_n$H$_{2n}$— | Vn— |
| C$_n$H$_{2n+1}$CH=CHC$_m$H$_{2m}$— | nVm— |
| C$_n$H$_{2n+1}$CH=CHC$_m$H$_{2m}$CH=CHC$_k$H$_{2k}$— | nVmVk— |
| 2) Ring structure —(A$_1$)—, —(A$_n$)— | Symbol |

TABLE 1-continued

Method for designating compounds by using symbols
R—(A₁)—Z₁—...—Zₙ—(Aₙ)—X

| | Symbol |
|---|---|
|  | B |
| 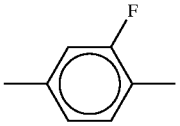 | B(F) |
| 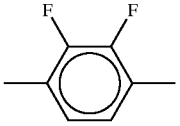 | B(2F,3F) |
| 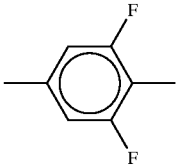 | B(F,F) |
|  | H |
| 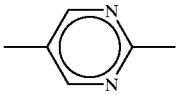 | Py |
|  | G |
| 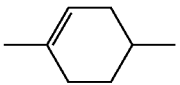 | Ch |

| 3) Bonding group —Z₁—, —Zₙ— | Symbol |
|---|---|
| —C₂H₄— | 2 |
| —C₄H₈— | 4 |
| —COO— | E |
| —C≡C— | T |
| —CH=CH— | V |
| —CF₂O— | CF2O |
| —OCF₂— | OCF₂ |

| 4) Right side terminal group —X | Symbol |
|---|---|
| —F | —F |
| —Cl | —CL |
| —Br | —Br |
| —CN | —C |
| —CF₃ | —CF3 |
| —OCF₃ | —OCF3 |
| —OCF₂H | —OCF2H |
| —CₙH₂ₙ₊₁ | —n |
| —OCₙH₂ₙ₊₁ | —On |
| —COOCH₃ | —EMe |
| —CₙH₂ₙCH=CH₂ | —nV |
| —CₘH₂ₘCH=CHCₙH₂ₙ₊₁ | —mVn |
| —CₘH₂ₘCH=CHCₙH₂ₙF | —mVnF |
| —CH=CF₂ | —VFF |
| —CₙH₂ₙCH=CF₂ | —nVFF |
| —C≡C—CN | —TC |

5) Examples of designation

Example 1    3-H2B(F,F)B(F)—F

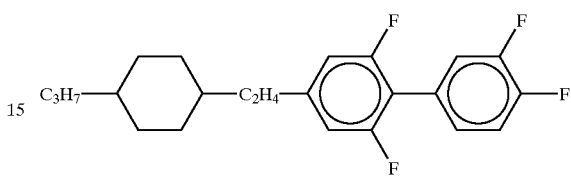

Example 2    3-HB(F)TB-2

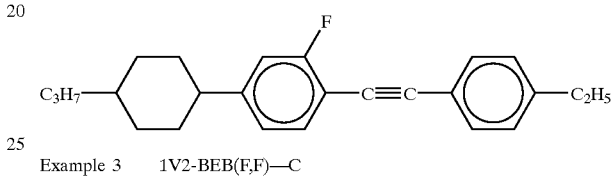

Example 3    1V2-BEB(F,F)—C

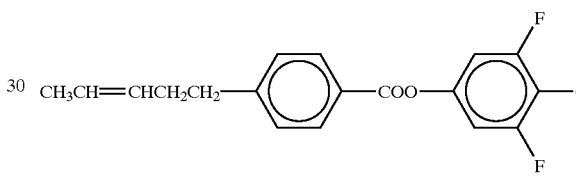

Use Example 1

| | |
|---|---|
| 3N-BEB(F)-Br | 10.0% |
| 1V2-BEB(F, F)-C | 5.0% |
| 3-HB-C | 20.0% |
| 1-BTB-3 | 5.0% |
| 2-BTB-1 | 10.0% |
| 3-HH-4 | 6.0% |
| 3-HHB-1 | 11.0% |
| 3-HHB-3 | 9.0% |
| 3-H2BTB-2 | 4.0% |
| 3-H2BTB-3 | 4.0% |
| 3-H2BTB-4 | 4.0% |
| 3-HB(F)TB-2 | 6.0% |
| 3-HB(F)TB-3 | 6.0% |
| NI = 88.0 (° C.) | |
| η = 28.8 (mPa · s) | |
| Δn = 0.174 | |
| Δε = 11.1 | |
| Vth = 1.90 (V) | |

The pitch was 10.5 μm on the liquid crystal composition prepared by the addition of 0.8 part by weight of the optically active compound (C-4) to 100 part by weight of the liquid crystal composition above.

Use Example 2

| | |
|---|---|
| 3N-BEB(F)-Br | 5.0% |
| 2O1-BEB(F)-C | 5.0% |
| 3O1-BEB(F)-C | 15.0% |

-continued

| | |
|---|---|
| 4O1-BEB (F)-C | 13.0% |
| 5O1-BEB (F)-C | 8.0% |
| 2-HHB(F)-C | 15.0% |
| 3-HHB(F)-C | 15.0% |
| 3-HB(F)TB-2 | 4.0% |
| 3-HB(F)TB-3 | 4.0% |
| 3-HB(F)TB-4 | 4.0% |
| 3-HHB-1 | 8.0% |
| 3-HHB-O1 | 4.0% |

NI = 93.8 (° C.)
η = 89.9 (mPa · s)
Δn = 0.155
Δε = 32.0
Vth = 0.85 (V)

Use Example 3

| | |
|---|---|
| 3N(1)-B(F, F)EB(F, F)-C | 3.0% |
| 4N(1)-B(F, F)EB(F, F)-C | 3.0% |
| 5N(1)-B(F, F)EB(F, F)-C | 3.0% |
| 5-PyB-F | 4.0% |
| 3-PyB(F)-F | 4.0% |
| 2-BB-C | 5.0% |
| 4-BB-C | 4.0% |
| 5-BB-C | 5.0% |
| 2-PyB-2 | 2.0% |
| 3-PyB-2 | 2.0% |
| 4-PyB-2 | 2.0% |
| 6-PyB-O5 | 3.0% |
| 6-PyB-O6 | 3.0% |
| 6-PyB-O7 | 3.0% |
| 6-PyB-O8 | 3.0% |
| 3-PyBB-F | 3.0% |
| 4-PyBB-F | 3.0% |
| 5-PyBB-F | 3.0% |
| 3-HHB-1 | 6.0% |
| 3-HHB-3 | 8.0% |
| 2-H2BTB-2 | 4.0% |
| 2-H2BTB-3 | 4.0% |
| 2-H2BTB-4 | 5.0% |
| 3-H2BTB-2 | 5.0% |
| 3-H2BTB-3 | 5.0% |
| 3-H2BTB-4 | 5.0% |

Use Example 4

| | |
|---|---|
| 3N(1)-B(F, F)EB(F, F)-C | 3.0% |
| 4N(1)-B(F, F)EB(F, F)-C | 3.0% |
| 5N(1)-B(F, F)EB(F, F)-C | 3.0% |
| 3N-BEB(F)-C | 5.0% |
| 3-DB-C | 5.0% |
| 4-DB-C | 5.0% |
| 2-BEB-C | 8.0% |
| 3-BEB-C | 4.0% |
| 3-PyB(F)-F | 6.0% |
| 3-HEB-O4 | 8.0% |
| 4-HEB-O2 | 6.0% |
| 5-HEB-O1 | 6.0% |
| 3-HEB-O2 | 5.0% |
| 5-HEB-O2 | 4.0% |
| 5-HEB-5 | 5.0% |
| 4-HEB-5 | 5.0% |
| 1O-BEB-2 | 4.0% |
| 3-HHB-1 | 6.0% |
| 3-HHEBB-C | 3.0% |
| 3-HBEBB-C | 3.0% |
| 5-HBEBB-C | 3.0% |

Use Example 5

| | |
|---|---|
| 3N(1)-B(F, F)EB(F, F)-C | 3.0% |
| 3-HB-C | 18.0% |
| 7-HB-C | 3.0% |
| 1O1-HB-C | 10.0% |
| 3-HB(F)-C | 7.0% |
| 2-PyB-2 | 2.0% |
| 3-PyB-2 | 2.0% |
| 4-PyB-2 | 2.0% |
| 1O1-HH-3 | 7.0% |
| 2-BTB-O1 | 7.0% |
| 3-HHB-1 | 7.0% |
| 3-HHB-F | 4.0% |
| 3-HHB-O1 | 4.0% |
| 3-HHB-3 | 8.0% |
| 3-H2BTB-2 | 3.0% |
| 3-H2BTB-3 | 3.0% |
| 2-PyBH-3 | 4.0% |
| 3-PyBH-3 | 3.0% |
| 3-PyBB-2 | 3.0% |

NI = 77.4 (° C.)
η = 20.2 (mPa · s)
Δn = 0.142
Δε = 9.9
Vth = 1.70 (V)

Use Example 6

| | |
|---|---|
| 3N-BEB(F)-C | 9.0% |
| 2O1-BEB(F)-C | 5.0% |
| 3O1-BEB(F)-C | 6.0% |
| 5O1-BEB(F)-C | 4.0% |
| 1V2-BEB(F, F)-C | 10.0% |
| 3-HH-EMe | 10.0% |
| 3-HB-O2 | 18.0% |
| 7-HEB-F | 2.0% |
| 3-HHEB-F | 2.0% |
| 5-HHEB-F | 2.0% |
| 3-HBEB-F | 4.0% |
| 2O1-HBEB(F)-C | 2.0% |
| 3-HB(F)EB(F)-C | 2.0% |
| 3-HBEB(F, F)-C | 2.0% |
| 3-HHB-F | 4.0% |
| 3-HHB-O1 | 4.0% |
| 3-HHB-3 | 10.0% |
| 3-HEBEB-F | 2.0% |
| 3-HEBEB-1 | 2.0% |

NI = 76.5 (° C.)
η = 45.0 (mPa · s)
Δn = 0.124
Δε = 26.9
Vth = 0.96 (V)

Use Example 7

| | |
|---|---|
| 3N-BEB(F)-C | 12.0% |
| 2O1-BEB(F)-C | 5.0% |
| 3O1-BEB(F)-C | 3.0% |
| 5O1-BEB(F)-C | 4.0% |
| 1V2-BEB(F, F)-C | 16.0% |
| 3-HB-O2 | 10.0% |
| 3-HH-4 | 3.0% |
| 3-HHB-F | 3.0% |
| 3-HHB-1 | 6.0% |
| 3-HHB-O1 | 3.0% |
| 3-HBEB-F | 4.0% |
| 3-HHEB-F | 7.0% |
| 5-HHEB-F | 7.0% |
| 3-H2BTB-2 | 4.0% |

-continued

| | |
|---|---|
| 3-H2BTB-3 | 4.0% |
| 3-H2BTB-4 | 4.0% |
| 3-HB(F)TB-2 | 5.0% |
| NI = 90.5 (° C.) | |
| η = 53.5 (mPa · s) | |
| Δn = 0.154 | |
| Δε = 30.8 | |
| Vth = 0.98 (V) | |

Use Example 8

| | |
|---|---|
| 3N-BEB(F)-Br | 7.0% |
| 2-BEB-C | 10.0% |
| 5-BB-C | 8.0% |
| 7-BB-C | 4.0% |
| 1-BTB-3 | 7.0% |
| 2-BTB-1 | 10.0% |
| 1O-BEB-2 | 10.0% |
| 1O-BEB-5 | 12.0% |
| 2-HHB-1 | 4.0% |
| 3-HHB-F | 4.0% |
| 3-HHB-1 | 7.0% |
| 3-HHB-O1 | 4.0% |
| 3-HHB-3 | 13.0% |
| NI = 66.0 (° C.) | |
| η = 28.0 (mPa · s) | |
| Δn = 0.161 | |
| Δε = 9.0 | |
| Vth = 1.68 (V) | |

Use Example 9

| | |
|---|---|
| 3N(1)-B(F, F)EB(F, F)-C | 3.0% |
| 4N(1)-B(F, F)EB(F, F)-C | 3.0% |
| 5N(1)-B(F, F)EB(F, F)-C | 3.0% |
| 2-HB-C | 5.0% |
| 3-HB-C | 9.0% |
| 3-HB-O2 | 15.0% |
| 2-BTB-1 | 3.0% |
| 3-HHB-1 | 8.0% |
| 3-HHB-F | 4.0% |
| 3-HHB-O1 | 5.0% |
| 3-HHB-3 | 8.0% |
| 3-HHEB-F | 4.0% |
| 5-HHEB-F | 4.0% |
| 2-HHB(F)-F | 7.0% |
| 3-HHB(F)-F | 7.0% |
| 5-HHB(F)-F | 7.0% |
| 3-HHB(F, F)-F | 5.0% |

Use Example 10

| | |
|---|---|
| 3N-BEB(F)-C | 3.0% |
| 3-BEB(F)-C | 8.0% |
| 3-HB-C | 5.0% |
| V-HB-C | 8.0% |
| 1V-HB-C | 8.0% |
| 3-HB-O2 | 3.0% |
| 3-HH-2V | 14.0% |
| 3-HH-2V1 | 7.0% |
| V2-HHB-1 | 15.0% |
| 3-HHB-1 | 5.0% |
| 3-HHEB-F | 7.0% |
| 3-H2BTB-2 | 6.0% |
| 3-H2BTB-3 | 6.0% |
| 3-H2BTB-4 | 5.0% |
| NI = 98.9 (° C.) | |
| η = 20.0 (mPa · s) | |
| Δn = 0.135 | |
| Δε = 9.5 | |
| Vth = 2.13 (V) | |

Use Example 11

| | |
|---|---|
| 3N-BEB(F)-Br | 10.0% |
| 3N(1)-B(F, F)EB(F, F)-C | 3.0% |
| 4N(1)-B(F, F)EB(F, F)-C | 3.0% |
| 5N(1)-B(F, F)EB(F, F)-C | 3.0% |
| 3N-BEB(F)-C | 10.0% |
| V2-HB-C | 5.0% |
| 1V2-HB-C | 5.0% |
| 3-HB-C | 19.0% |
| 3-HB(F)-C | 5.0% |
| 2-BTB-1 | 2.0% |
| 3-HH-4 | 3.0% |
| 3-HH-VFF | 6.0% |
| 2-HHB-C | 3.0% |
| 3-HHB-C | 6.0% |
| 3-HB(F)TB-2 | 8.0% |
| 3-H2BTB-2 | 3.0% |
| 3-H2BTB-3 | 3.0% |
| 3-H2BTB-4 | 3.0% |

Use Example 12

| | |
|---|---|
| 3N(1)-B(F, F)EB(F, F)-C | 3.0% |
| 5-BEB(F)-C | 2.0% |
| V-HB-C | 11.0% |
| 5-PyB-C | 6.0% |
| 4-BB-3 | 11.0% |
| 3-HH-2V | 10.0% |
| 5-HH-V | 11.0% |
| V-HHB-1 | 7.0% |
| V2-HHB-1 | 15.0% |
| 3-HHB-1 | 9.0% |
| 1V2-HBB-2 | 10.0% |
| 3-HHEBH-3 | 5.0% |
| NI = 89.3 (° C.) | |
| η = 17.0 (mPa · s) | |
| Δn = 0.116 | |
| Δε = 6.3 | |
| Vth = 2.25 (V) | |

Use Example 13

| | |
|---|---|
| 3N-BEB(F)-Br | 4.0% |
| 1V2-BEB(F, F)-C | 8.0% |
| 3-HB-C | 8.0% |
| V2V-HB-C | 14.0% |
| V2V-HH-3 | 17.0% |
| 3-HB-O2 | 4.0% |
| 3-HHB-1 | 10.0% |
| 3-HHB-3 | 15.0% |
| 3-HB(F)TB-2 | 4.0% |
| 3-HB(F)TB-3 | 4.0% |
| 3-H2BTB-2 | 4.0% |
| 3-H2BTB-3 | 4.0% |
| 3-H2BTB-4 | 4.0% |
| NI = 100.0 (° C.) | |
| η = 22.5 (mPa · s) | |

-continued

Δn = 0.135
Δε = 9.5
Vth = 1.95 (V)

Use Example 14

| | |
|---|---|
| 3N-BEB(F)-C | 7.0% |
| V2-HB-TC | 10.0% |
| 3-HB-TC | 10.0% |
| 3-HB-C | 6.0% |
| 5-HB-C | 4.0% |
| 5-BB-C | 3.0% |
| 2-BTB-1 | 10.0% |
| 2-BTB-O1 | 5.0% |
| 3-HH-4 | 5.0% |
| 3-HHB-1 | 10.0% |
| 3-HHB-3 | 11.0% |
| 3-H2BTB-2 | 3.0% |
| 3-H2BTB-3 | 3.0% |
| 3-HB(F)TB-2 | 3.0% |
| 5-BTB(F)TB-2 | 10.0% |

NI = 100.7 (° C.)
η = 23.4 (mPa · s)
Δn = 0.212
Δε = 9.5
Vth = 1.92 (V)

Use Example 15

| | |
|---|---|
| 3N(1)-B(F, F)EB(F, F)-C | 3.0% |
| 1V2-BEB(F, F)-C | 3.0% |
| 3-HB-C | 18.0% |
| 2-BTB-1 | 10.0% |
| 5-HH-VFF | 30.0% |
| 1-BHH-VFF | 8.0% |
| 1-BHH-2VFF | 11.0% |
| 3-H2BTB-2 | 5.0% |
| 3-H2BTB-3 | 4.0% |
| 3-H2BTB-4 | 4.0% |
| 3-HHB-1 | 4.0% |

NI = 79.5 (° C.)
η = 13.3 (mPa · s)
Δn = 0.130
Δε = 7.5
Vth = 1.98 (V)

Use Example 16

| | |
|---|---|
| 3N-BEB(F)-Br | 5.0% |
| 2-HHB(F)-F | 17.0% |
| 3-HHB(F)-F | 17.0% |
| 5-HHB(F)-F | 16.0% |
| 2-H2HB(F)-F | 10.0% |
| 3-H2HB(F)-F | 5.0% |
| 5-H2HB(F)-F | 5.0% |
| 2-HBB(F)-F | 6.0% |
| 3-HBB(F)-F | 6.0% |
| 5-HBB(F)-F | 13.0% |

NI = 96.5 (° C.)
η = 31.2 (mPa · s)
Δn = 0.099
Δε = 7.1
Vth = 2.04 (V)

The pitch was 76 μm on the liquid crystal composition prepared by the addition of 0.3 part by weight of the optically active compound (C-8) to 100 part by weight of the liquid crystal composition above.

Use Example 17

| | |
|---|---|
| 3N(1)-B(F, F)EB(F, F)-C | 3.0% |
| 4N(1)-B(F, F)EB(F, F)-C | 3.0% |
| 5N(1)-B(F, F)EB(F, F)-C | 3.0% |
| 3N-BEB(F)-C | 5.0% |
| 3-HB-CL | 10.0% |
| 5-HB-CL | 4.0% |
| 7-HB-CL | 4.0% |
| 1O1-HH-5 | 5.0% |
| 2-HBB(F)-F | 8.0% |
| 3-HBB(F)-F | 4.0% |
| 5-HBB(F)-F | 4.0% |
| 4-HHB-CL | 8.0% |
| 5-HHB-CL | 8.0% |
| 3-H2HB(F)-CL | 4.0% |
| 3-HBB(F, F)-F | 10.0% |
| 5-H2BB(F, F)-F | 9.0% |
| 3-HB(F)VB-2 | 4.0% |
| 3-HB(F)VB-3 | 4.0% |

Use Example 18

| | |
|---|---|
| 3N-BEB(F)-Br | 8.0% |
| 3-HHB(F, F)-F | 9.0% |
| 3-H2HB(F, F)-F | 8.0% |
| 4-H2HB(F, F)-F | 4.0% |
| 5-H2HB(F, F)-F | 4.0% |
| 3-HBB(F, F)-F | 21.0% |
| 5-HBB(F, F)-F | 20.0% |
| 3-H2BB(F, F)-F | 10.0% |
| 5-HHBB(F, F)-F | 3.0% |
| 5-HHEBB-F | 2.0% |
| 3-HH2BB(F, F)-F | 3.0% |
| 1O1-HBBH-4 | 4.0% |
| 1O1-HBBH-5 | 4.0% |

NI = 94.1 (° C.)
η = 43.8 (mPa · s)
Δn = 0.127
Δε = 12.0
Vth = 1.66 (V)

The pitch was 61 μm on the liquid crystal composition prepared by the addition of 0.25 part by weight of the optically active compound (C-5) to 100 part by weight of the liquid crystal composition above.

Use Example 19

| | |
|---|---|
| 3N-BEB(F)-C | 10.0% |
| 5-HB-F | 12.0% |
| 6-HB-F | 9.0% |
| 7-HB-F | 7.0% |
| 2-HHB-OCF3 | 7.0% |
| 3-HHB-OCF3 | 7.0% |
| 4-HHB-OCF3 | 7.0% |
| 5-HHB-OCF3 | 5.0% |
| 3-HH2B-OCF3 | 4.0% |
| 5-HH2B-OCF3 | 4.0% |
| 3-HHB(F, F)-OCF3 | 5.0% |
| 3-HBB(F)-F | 5.0% |
| 5-HBB(F)-F | 5.0% |
| 3-HH2B(F)-F | 3.0% |
| 3-HB(F)BH-3 | 3.0% |
| 5-HBBH-3 | 3.0% |

-continued

| | |
|---|---|
| 3-HHB(F, F)-OCF2H | 4.0% |

Use Example 20

| | |
|---|---|
| 3N(1)-B(F, F)EB(F, F)-C | 3.0% |
| 7-HB(F)-F | 5.0% |
| 5-H2B(F)-F | 5.0% |
| 3-HB-O2 | 10.0% |
| 3-HH-4 | 5.0% |
| 2-HHB(F)-F | 10.0% |
| 3-HHB(F)-F | 10.0% |
| 5-HHB(F)-F | 10.0% |
| 3-H2HB(F)-F | 5.0% |
| 2-HBB(F)-F | 3.0% |
| 5-HBB(F)-F | 6.0% |
| 2-H2BB(F)-F | 5.0% |
| 3-H2BB(F)-F | 6.0% |
| 3-HHB-1 | 8.0% |
| 3-HHB-O1 | 5.0% |
| 3-HHB-3 | 4.0% |

Use Example 21

| | |
|---|---|
| 3N-BEB(F)-Br | 5.0% |
| 7-HB(F, F)-F | 3.0% |
| 3-H2HB(F, F)-F | 12.0% |
| 4-H2HB(F, F)-F | 10.0% |
| 5-H2HB(F, F)-F | 10.0% |
| 4-HHB(F, F)-F | 5.0% |
| 3-HH2B(F, F)-F | 15.0% |
| 5-HH2B(F, F)-F | 10.0% |
| 3-HBB(F, F)-F | 12.0% |
| 5-HBB(F, F)-F | 12.0% |
| 3-HBCF2OB(F, F)-F | 6.0% |
| NI = 70.4 (° C.) | |
| η = 31.6 (mPa · s) | |
| Δn = 0.092 | |
| Δε = 10.6 | |
| Vth = 1.48 (V) | |

Use Example 22

| | |
|---|---|
| 3N(1)-B(F, F)EB(F, F)-C | 3.0% |
| 7-HB(F, F)-F | 5.0% |
| 3-H2HB(F, F)-F | 12.0% |
| 4-H2HB(F, F)-F | 10.0% |
| 3-HHB(F, F)-F | 10.0% |
| 4-HHB(F, F)-F | 5.0% |
| 3-HBB(F, F)-F | 10.0% |
| 3-HHEB(F, F)-F | 10.0% |
| 4-HHEB(F, F)-F | 3.0% |
| 5-HHEB(F, F)-F | 3.0% |
| 2-HBEB(F, F)-F | 3.0% |
| 3-HBEB(F, F)-F | 5.0% |
| 3-HDB(F, F)-F | 15.0% |
| 3-HHBB(F, F)-F | 6.0% |
| NI = 71.4 (° C.) | |
| η = 36.0 (mPa · s) | |
| Δn = 0.085 | |
| Δε = 15.3 | |
| Vth = 1.32 (V) | |

Use Example 23

| | |
|---|---|
| 3N-BEB(F)-Br | 4.0% |
| 5-H4HB(F, F)-F | 7.0% |
| 5-H4HB-OCF3 | 15.0% |
| 3-H4HB(F, F)-CF3 | 8.0% |
| 5-H4HB(F, F)-CF3 | 10.0% |
| 3-HB-CL | 6.0% |
| 2-H2BB(F)-F | 5.0% |
| 3-H2BB(F)-F | 10.0% |
| 5-HVHB(F, F)-F | 5.0% |
| 3-HHB-OCF3 | 5.0% |
| 3-H2HB-OCF3 | 5.0% |
| V-HHB(F)-F | 5.0% |
| 3-HHB(F)-F | 5.0% |
| 5-HHEB-OCF3 | 2.0% |
| 3-HBEB(F, F)-F | 5.0% |
| 5-HH-V2F | 3.0% |
| NI = 70.0 (° C.) | |
| η = 30.9 (mPa · s) | |
| Δn = 0.099 | |
| Δε = 9.9 | |
| Vth = 1.67 (V) | |

METHOD OF PRERARATION

The compound of the present invention is synthesized by the following method.

SYNTHETIC METHOD 1

When Za, Zb, and Zc are a single bond, 1, 2-ethynylene, or oxymethylene

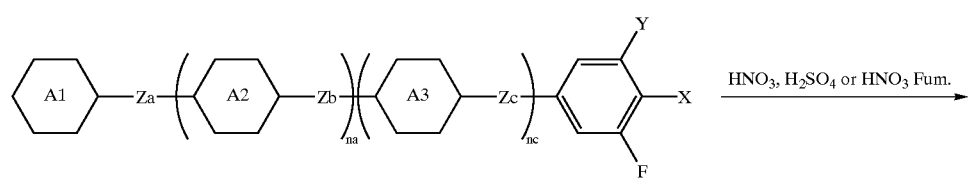

(13)

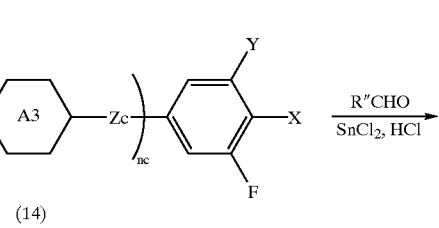

(14)

-continued
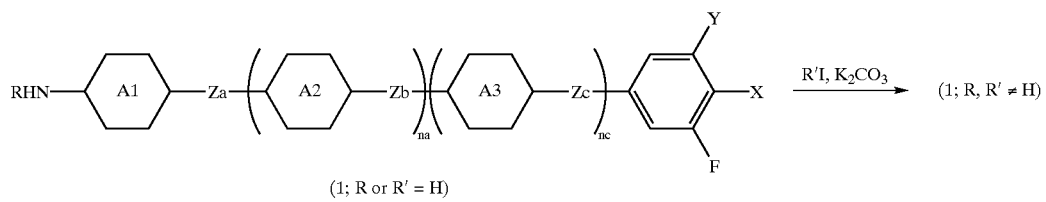
When R = R' = H
SYNTHETIC METHOD 2
When Za is COO
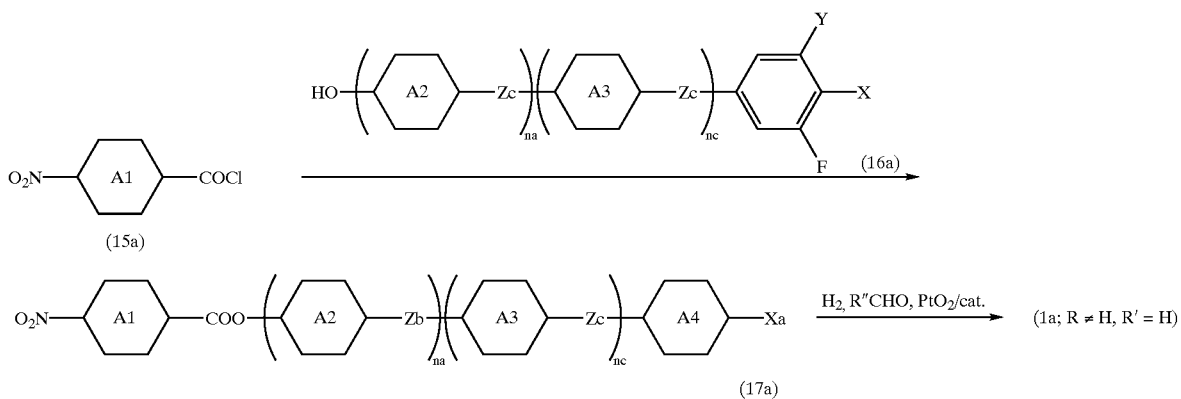
When Zb is COO
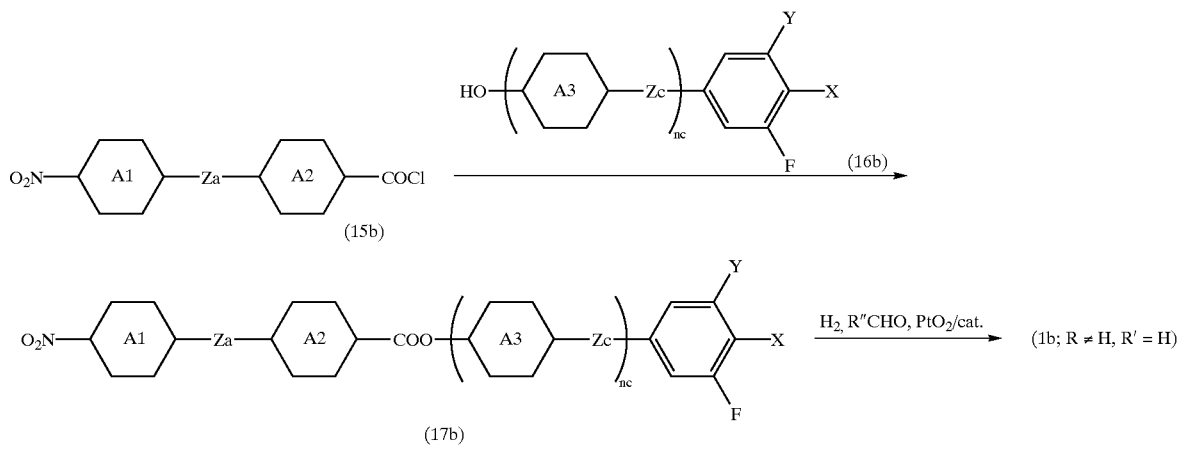
When Zc is COO
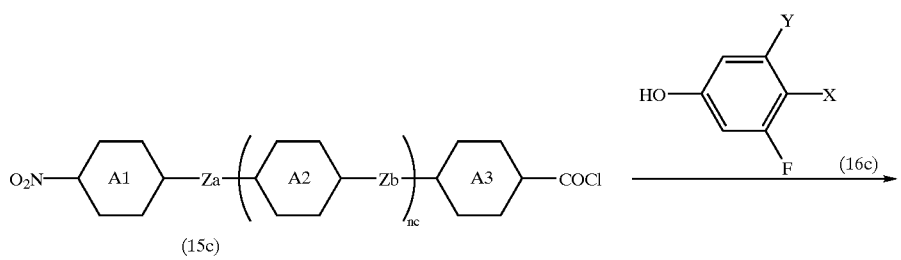

-continued

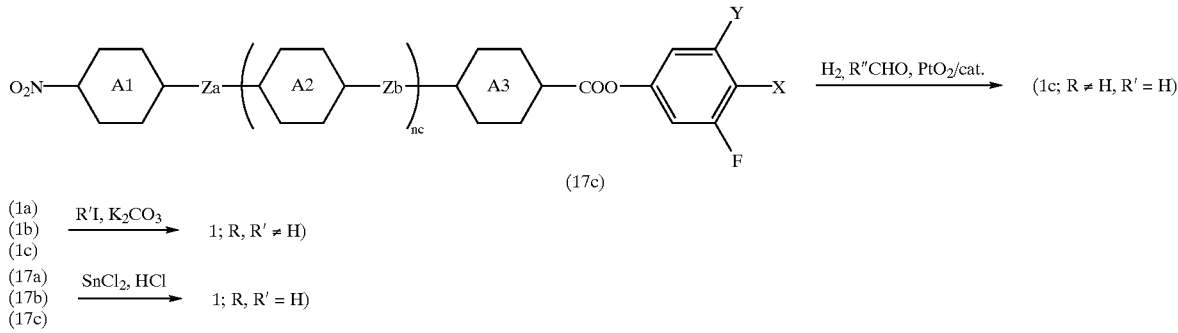

(1a)
(1b)  $\xrightarrow{R'I, K_2CO_3}$  1; R, R' ≠ H)
(1c)

(17a)
(17b)  $\xrightarrow{SnCl_2, HCl}$  1; R, R' = H)
(17c)

wherein R, X, A1, A2, A3, Za, Zb, and Zc represent the same with the meaning described above unless otherwise noted. R" represents alkyl having one less carbon number than the carbon number of R, provided that R" represents hydrogen when R is methyl.

SYNTHETIC METHOD 1

Synthesis of a compound in which Za, Zb, and Zc are independently each other a single bond, 1,2-ethylene, or oxymethylene.

In the compound that Zb is a single bond, 1,2-ethylene, or oxymethylene in general formula (1), the compound of general formula (1) with R' being H can be prepared by the nitration of the compound represented by formula (13) with mixed acid or fumed nitric acid to give the compound of formula (14) and then by the treatment under the reduction conditions, as is shown in SYNTHETIC METHOD 1. The compound of general formula (1) in which both R and R' is not H can be prepared by the reaction of the compound with R' being H thus prepared, with R'I under the basic conditions.

The compound in which both R and R' are hydrogen simultaneously can easily be prepared by the reduction of the compound of formula (14) in the absence of R"CHO. Each of the compound represented by the formula (13) can easily be prepared by the combination of methods known to a person skilled in the art.

SYNTHETIC METHOD 2

The compound that any of or some of Za, Zb, and Zc are an ester bond and any one of R and R' is hydrogen in formula (1), can be obtained by the reaction of a carboxylic acid or a carboxylic acid chloride represented by formulae (15a) to (15c) with a phenol or an alcohol represented by formula (16a) to (16c) to give an ester derivative represented by formulae (19a) to (19c), and then by the treatment with an aldehyde under the hydrogenation conditions in the presence of a proper catalyst such as platinum oxide.

The compound in which both R and R' are not hydrogen can be obtained by the alkylation of the compound in which any one of R or R' is hydrogen, with the combination of a base such as potasium carbonate and an alkylating agent such as alkyl halide.

The compound in which both R and R' are hydrogen can be prepared by the treatment of the compound represented by formula (17) with a reducing agent such as tin chloride under the reduction conditions.

The compound represented by formulae (15a) to (15c) and formulae (16a) to (16c) is commercially available or can easily be prepared by a person skilled in the art based on the combination of known methods.

EXAMPLES

The present invention is further explained in detail by the following examples, and the compound of the present invention is not limited to the examples.

Example 1

Synthesis of 4-Bromo-3-fluorophenyl 4-propylaminobenzoate

4-Nitrobenzoic acid chloride (0.1 mol) and 3-fuluoro-4-bromophenol (0.1 mol) was dissolved in dichloromenthane, and pyridine (0.1 mol) was added with stirring under ice-chilled conditions. After the addition, the reaction mixture was stirred for another 2 hours. Water was added to the reaction mixture and the product was extracted with dichloromethane. The organic layer obtained was washed with water, dried over anhydrous magnesium sulfate, and then concentrated under reduced pressure to give paleyellow solid. Recrystallization from toluene gave colorless crystals. The crystals were confirmed to be 4-bromo-3-fluorophenyl 4-nitrobenzoate as a result of various spectral data.

4-Bromo-3-fluorophenyl 4-nitrobenzoate was dissolved in toluene, and propion aldehyde and platinum oxide were added and stirred for 3 hours under an atmosphere of hydrogen. After the reaction, insoluble materials were filtered off, and the filtrate was concentrated under reduced pressure to give pale yellow crystals. Recrystallization from ether gave colorless solid (0.037 mmol, 12.3 g, m.p. 71.2° C.). The solid was confirmed to be the titled compound as a result of various spectral data.

Example 2

Synthesis of 4-Cyano-3-fluorophenyl 4-propylaminobenzoate

4-Cyano-3-fluorophenyl 4-nitrobenzoate (50 mmol), propanal (50 mmol), and platinum oxide (2 mmol) were dissolved in toluene (100 ml) and were stirred under an atmosphere of hydrogen at room temperature for 8 hours. After reaction, water was added to the reaction mixture, and the products were extracted with dichloromethane (50 ml, three times). The organic layer obtained was washed with water, dried over anhydrous magnesium sulfate, and then concentrated under reduced pressure to give brown oil. The oil was purified with silica gel chromatography and the pale yellow oil obtained was recrystallized from toluene to give colorless crystals (10 mmol). The crystals were confirmed to be the titled compound as a result of various spectral data.

Example 3

Synthesis of 3,5-Difluoro-4-cyanophenyl 2,4-difluoro-4-N-methyl-N-propylaminobenzoate 2,4-Difluoro-4-N-methyl-N-propylaminobenzoic acid (50 mmol) and dicyclohexylcarbodiimide (51 mmol) were dissolved in tetrahydrofuran (100 ml), and a tetrahydroduran solution (100 ml) of 3,5-difluoro-4-cyanophenol was added with stirring under ice cooled conditions. Triethylamine (50 mmol) was added to the solution and warmed up to room temperature after the stirring for 2 hours under ice chilled conditions. Insoluble materials formed were removed by filtration. The filtrate was concentrated under reduced pressure and was purified with column chromatography to give colorless crystals (12 mmol, mp 113.2° C.). The crystals were confirmed to be the titled compound as a result of various spectral data.

The following compounds are prepared according to the methods in EXAMPLE 1, 2, and 3.

| No. | R | R' | A1 | Za | na | A2 | Zb | nc | A3 | Zc | Y | Xa |
|---|---|---|---|---|---|---|---|---|---|---|---|---|
| 1 | CH$_3$ | H |  | — | 0 | — | — | 0 | — | — | H | F |
| 2 | C$_2$H$_5$ | CH$_3$ |  | — | 0 | — | — | 0 | — | — | F | F |
| 3 | C$_3$H$_7$ | H |  | — | 0 | — | — | 0 | — | — | H | F |
| 4 | n-C$_4$H$_9$ | H | 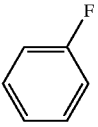 | — | 0 | — | — | 0 | — | — | F | OCF$_3$ |
| 5 | n-C$_5$H$_{11}$ | H |  | — | 0 | — | — | 0 | — | — | H | F |
| 6 | CH$_3$ | H |  | — | 0 | — | — | 0 | — | — | F | OCF$_3$ |
| 7 | C$_2$H$_5$ | H |  | — | 0 | — | — | 0 | — | — | H | Cl |
| 8 | C$_3$H$_7$ | CH$_3$ |  | — | 0 | — | — | 0 | — | — | F | Cl |
| 9 | n-C$_4$H$_9$ | H |  | — | 0 | — | — | 0 | — | — | H | Cl |
| 10 | n-C$_5$H$_{11}$ | H |  | — | 0 | — | — | 0 | — | — | F | Cl |
| 11 | CH$_3$ | H |  | — | 0 | — | — | 0 | — | — | H | Br |
| 12 | C$_2$H$_5$ | H |  | — | 0 | — | — | 0 | — | — | F | Br |

-continued
| No. | R | R' | A1 | Za | na | A2 | Zb | nc | A3 | Zc | Y | X |
|---|---|---|---|---|---|---|---|---|---|---|---|---|
| 13 | C$_3$H$_7$ | H |  | — | 0 | — | — | 0 | — | — | H | Br |
| 14 | C$_2$H$_5$OCH$_2$ | H |  | — | 0 | — | — | 0 | — | — | F | I |
| 15 | n-C$_5$H$_{11}$ | H | 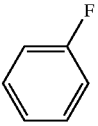 | — | 0 | — | — | 0 | — | — | H | I |
| 16 | CH$_3$ | H | 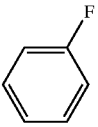 | — | 0 | — | — | 0 | — | — | F | CN |
| 17 | C$_2$H$_5$ | H |  | — | 0 | — | — | 0 | — | — | H | CN |
| 18 | C$_3$H$_7$ | H |  | — | 0 | — | — | 0 | — | — | F | 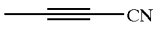 |
| 19 | n-C$_4$H$_9$ | H |  | — | 0 | — | — | 0 | — | — | H | 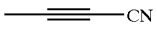 |
| 20 | n-C$_5$H$_{11}$ | H |  | — | 0 | — | — | 0 | — | — | F | 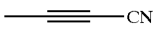 |
| 21 | CH$_3$ | H |  | COO | 0 | — | — | 0 | — | — | H | F |
| 22 | C$_2$H$_5$ | CH$_3$ |  | COO | 0 | — | — | 0 | — | — | F | F |
| 23 | C$_3$H$_7$ | H |  | COO | 0 | — | — | 0 | — | — | H | OCF$_3$ |
| 24 | CH$_3$OCH$_2$ | H |  | COO | 0 | — | — | 0 | — | — | F | CF$_3$ |
| 25 | n-C$_5$H$_{11}$ | H |  | COO | 0 | — | — | 0 | — | — | H | F |
| 26 | CH$_3$ | H |  | COO | 0 | — | — | 0 | — | — | F | Cl |

-continued
| No. | R | R' | A1 | Za | na | A2 | Zb | nc | A3 | Zc | Y | |
|---|---|---|---|---|---|---|---|---|---|---|---|---|
| 27 | C$_2$H$_5$ | H |  | COO | 0 | — | — | 0 | — | — | H | Cl |
| 28 | C$_3$H$_7$ | CH$_3$ |  | COO | 0 | — | — | 0 | — | — | F | Cl |
| 29 | n-C$_4$H$_9$ | H |  | COO | 0 | — | — | 0 | — | — | H | Cl |
| 30 | n-C$_5$H$_{11}$ | H |  | COO | 0 | — | — | 0 | — | — | F | Cl |
| 31 | CH$_3$ | H |  | COO | 0 | — | — | 0 | — | — | H | Br |
| 32 | C$_2$H$_5$ | H |  | COO | 0 | — | — | 0 | — | — | F | Br |
| 33 | C$_3$H$_7$ | H | 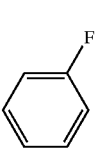 | COO | 0 | — | — | 0 | — | — | H | Br |
| 34 | n-C$_4$H$_9$ | CH$_3$ |  | COO | 0 | — | — | 0 | — | — | F | I |
| 35 | n-C$_5$H$_{11}$ | H |  | COO | 0 | — | — | 0 | — | — | H | I |
| 36 | CH$_3$ | H | 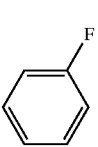 | COO | 0 | — | — | 0 | — | — | F | CN |
| 37 | C$_2$H$_5$ | H |  | COO | 0 | — | — | 0 | — | — | H | CN |
| 38 | C$_3$H$_7$ | H |  | COO | 0 | — | — | 0 | — | — | F | —CN |
| 39 | n-C$_4$H$_9$ | H |  | COO | 0 | — | — | 0 | — | — | H | —CN |
| 40 | n-C$_5$H$_{11}$ | H |  | COO | 0 | — | — | 0 | — | — | F | —CN |

-continued
| No. | R | R' | A1 | Za | na | A2 | Zb | nc | A3 | Zc | Y | Xa |
|---|---|---|---|---|---|---|---|---|---|---|---|---|
| 41 | CH$_3$ | H |  | — | 1 |  | — | 0 | — | — | H | F |
| 42 | C$_2$H$_5$ | CH$_3$ |  | — | 1 |  | — | 0 | — | — | F | F |
| 43 | C$_3$H$_7$ | H |  | — | 1 |  | — | 0 | — | — | H | OCF$_3$ |
| 44 | n-C$_4$H$_9$ | H |  | — | 1 |  | — | 0 | — | — | F | F |
| 45 | n-C$_5$H$_{11}$ | H |  | — | 1 |  | — | 0 | — | — | H | F |
| 46 | CH$_3$ | CH$_3$ |  | — | 1 |  | — | 0 | — | — | F | Cl |
| 47 | C$_2$H$_5$ | H |  | — | 1 |  | — | 0 | — | — | H | CF$_3$ |
| 48 | C$_3$H$_7$ | H |  | — | 1 |  | — | 0 | — | — | F | Cl |
| 49 | n-C$_4$H$_9$ | H |  | — | 1 |  | — | 0 | — | — | H | Cl |
| 50 | CH$_3$OCH$_2$ | H |  | — | 1 |  | — | 0 | — | — | F | Cl |
| 51 | CH$_3$ | H |  | — | 1 |  | — | 0 | — | — | H | Br |
| 52 | C$_2$H$_5$ | CH$_3$ |  | — | 1 |  | — | 0 | — | — | F | Br |
| 53 | C$_3$H$_7$ | H |  | COO | 1 |  | — | 0 | — | — | H | Br |
| 54 | n-C$_4$H$_9$ | H |  | — | 1 |  | — | 0 | — | — | F | I |
| 55 | n-C$_5$H$_{11}$ | H |  | — | 1 |  | — | 0 | — | — | H | I |

-continued
| No. | R | R' | A1 | Za | na | A2 | Zb | nc | A3 | Zc | Y | |
|---|---|---|---|---|---|---|---|---|---|---|---|---|
| 56 | CH₃ | CH₃ |  | — | 1 |  | — | 0 | — | — | F | CN |
| 57 | C₂H₅ | H |  | COO | 1 |  | — | 0 | — | — | H | CN |
| 58 | C₃H₇ | H |  | — | 1 |  | — | 0 | — | — | F | —CN |
| 59 | n-C₄H₉ | H |  | — | 1 |  | — | 0 | — | — | H | —CN |
| 60 | n-C₅H₁₁ | H |  | — | 1 |  | — | 0 | — | — | F | —CN |
| | | | | | | | | | | | | X |
| 61 | CH₃ | H |  | — | 1 |  | COO | 0 | — | — | H | F |
| 62 | C₂H₅ | CH₃ |  | — | 1 |  | COO | 0 | — | — | F | F |
| 63 | C₃H₇ | H |  | — | 1 |  | COO | 0 | — | — | H | F |
| 64 | n-C₄H₉ | H |  | — | 1 |  | COO | 0 | — | — | F | OCF₃ |
| 65 | n-C₅H₁₁ | H |  | — | 1 |  | COO | 0 | — | — | H | F |
| 66 | CH₃ | H |  | — | 1 |  | COO | 0 | — | — | F | Cl |
| 67 | C₂H₅ | H | 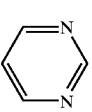 | — | 1 | 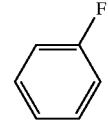 | COO | 0 | — | — | H | CF₃ |
| 68 | C₃H₇ | CH₃ |  | — | 1 |  | COO | 0 | — | — | F | Cl |
| 69 | n-C₄H₉ | H |  | — | 1 |  | COO | 0 | — | — | H | Cl |

-continued
| No. | R | R' | A1 | Za | na | A2 | Zb | nc | A3 | Zc | | Y |
|---|---|---|---|---|---|---|---|---|---|---|---|---|
| 70 | n-C$_5$H$_{11}$ | H |  | — | 1 |  | COO | 0 | — | — | F | Cl |
| 71 | CH$_3$ | H |  | — | 1 |  | COO | 0 | — | — | H | Br |
| 72 | C$_2$H$_5$ | CH$_3$ |  | — | 1 |  | COO | 0 | — | — | F | Br |
| 73 | C$_3$H$_7$ | H |  | — | 1 |  | COO | 0 | — | — | H | Br |
| 74 | n-C$_4$H$_9$ | H |  | — | 1 |  | COO | 0 | — | — | F | I |
| 75 | n-C$_5$H$_{11}$ | H |  | — | 1 |  | COO | 0 | — | — | H | I |
| 76 | CH$_3$ | H |  | — | 1 |  | COO | 0 | — | — | F | CN |
| 77 | C$_2$H$_5$ | H |  | — | 1 |  | COO | 0 | — | — | H | CN |
| 78 | C$_3$H$_7$ | CH$_3$ |  | — | 1 |  | COO | 0 | — | — | F | 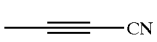 |
| 79 | n-C$_4$H$_9$ | H |  | — | 1 |  | COO | 0 | — | — | H | 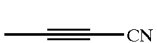 |
| 80 | n-C$_5$H$_{11}$ | H |  | — | 1 |  | COO | 0 | — | — | F |  |
| 81 | CH$_3$ | H |  | COO | 0 | — | — | 1 | 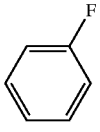 | — | H | F |
| 82 | C$_2$H$_5$ | CH$_3$ |  | COO | 0 | — | 1' | 1 |  | — | F | F |
| 83 | C$_3$H$_7$ | H | 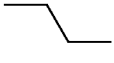 | COO | 0 | — | — | 1 |  | — | H | F |

-continued
| No. | R | R' | A1 | Za | na | A2 | Zb | nc | A3 | Zc | Y | |
|---|---|---|---|---|---|---|---|---|---|---|---|---|
| 84 | n-C$_4$H$_9$ | H |  | COO | 0 | — | — | 1 |  | — | F | F |
| 85 | n-C$_5$H$_{11}$ | H |  | COO | 0 | — | — | 1 |  | — | H | F |
| 86 | CH$_3$ | H |  | COO | 0 | — | — | 1 |  | — | F | Cl |
| 87 | C$_2$H$_5$ | H |  | COO | 0 | — | — | 1 | 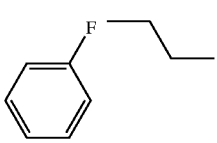 | — | H | Cl |
| 88 | C$_3$H$_7$ | CH$_3$ |  | COO | 0 | — | — | 1 |  | — | F | Cl |
| 89 | n-C$_4$H$_9$ | H |  | COO | 0 | — | — | 1 |  | — | H | Cl |
| 90 | n-C$_5$H$_{11}$ | H |  | COO | 0 | — | — | 1 |  | — | F | Cl |
| 91 | CH$_3$ | H |  | COO | 0 | — | — | 1 | 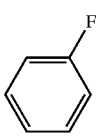 | — | H | Br |
| 92 | C$_2$H$_5$ | H |  | COO | 0 | — | — | 1 | 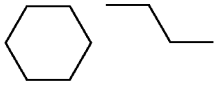 | — | F | Br |
| 93 | C$_3$H$_7$ | H |  | COO | 0 | — | — | 1 |  | — | H | Br |
| 94 | n-C$_4$H$_9$ | H |  | COO | 0 | — | — | 1 |  | — | F | I |
| 95 | n-C$_5$H$_{11}$ | H |  | COO | 0 | — | — | 1 |  | — | H | I |
| 96 | CH$_3$ | H |  | COO | 0 | — | — | 1 |  | — | F | CN |

-continued
| No. | R | R' | A1 | Za | na | A2 | Zb | nc | A3 | Zc | Y | |
|---|---|---|---|---|---|---|---|---|---|---|---|---|
| 97 | C₂H₅ | H |  | COO | 0 | — | — | 1 | 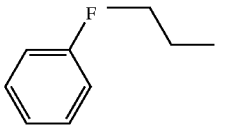 | | H | CN |
| 98 | C₃H₇ | CH₃ |  | COO | 0 | — | — | 1 |  | — | F | 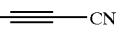—CN |
| 99 | n-C₄H₉ | H |  | COO | 0 | — | — | 1 |  | — | H | —CN |
| 100 | n-C₅H₁₁ | H |  | COO | 0 | — | — | 1 |  | — | F | —CN |
| 101 | CH₃ | H |  | — | 1 | 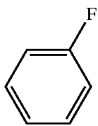 | COO | 1 | 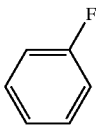 | — | H | F |
| 102 | C₂H₅ | CH₃ | 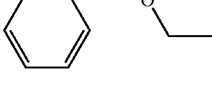 | | 1 |  | COO | 1 | 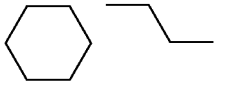 | | F | F |
| 103 | C₃H₇ | H |  | — | 1 |  | COO | 1 |  | — | H | F |
| 104 | n-C₄H₉ | H |  | — | 1 | 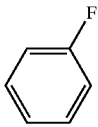 | COO | 1 |  | — | F | F |
| 105 | n-C₅H₁₁ | H |  | — | 1 | 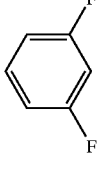 | COO | 1 |  | — | H | F |
| 106 | CH₃ | H |  | — | 1 |  | COO | 1 |  | — | F | Cl |
| 107 | C₂H₅ | H |  | — | 1 |  | COO | 1 | 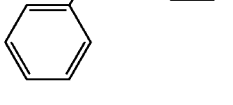 | | H | Cl |
| 108 | C₃H₇ | CH₃ | 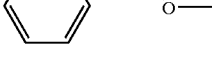 | | 1 |  | COO | 1 |  | — | F | Cl |

-continued
| No. | R | R' | A1 | Za | na | A2 | Zb | nc | A3 | Zc | Y | |
|---|---|---|---|---|---|---|---|---|---|---|---|---|
| 109 | n-C$_4$H$_9$ | H |  | — | 1 |  | COO | 1 |  | — | H | Cl |
| 110 | n-C$_5$H$_{11}$ | H |  | — | 1 |  | COO | 1 |  | — | F | Cl |
| 111 | CH$_3$ | H |  | — | 1 | 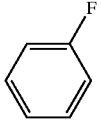 | COO | 1 | 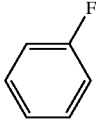 | — | H | Br |
| 112 | C$_2$H$_5$ | CH$_3$ |  | —O— | 1 |  | COO | 1 |  |  | F | Br |
| 113 | C$_3$H$_7$ | H |  | — | 1 | 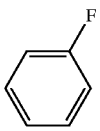 | COO | 1 |  | — | H | Br |
| 114 | n-C$_4$H$_9$ | H | 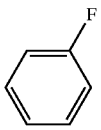 | — | 1 |  | COO | 1 |  | — | F | I |
| 115 | n-C$_5$H$_{11}$ | H | 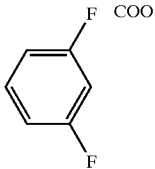 | — | 1 |  | COO | 1 |  | — | H | I |
| 116 | CH$_3$ | H |  | — | 1 |  | COO | 1 |  | — | F | CN |
| 117 | C$_2$H$_5$ | H |  | — | 1 | 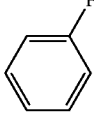 | COO | 1 |  | — | H | CN |
| 118 | C$_3$H$_7$ | CH$_3$ |  | —O— | 1 |  | COO | 1 |  | — | F | —≡—CN |
| 119 | n-C$_4$H$_9$ | H |  | — | 1 |  | COO | 1 |  | — | H | —≡—CN |
| 120 | n-C$_5$H$_{11}$ | H |  | — | 1 |  | COO | 1 | | — | F | —≡—CN |

-continued
| No. | R | R' | A1 | Za | na | A2 | Zb | nc | A3 | Zc | Y | |
|---|---|---|---|---|---|---|---|---|---|---|---|---|
| 121 | CH$_3$ | H |  | — | 1 |  | — | 1 |  | — | H | F |
| 122 | C$_2$H$_5$ | CH$_3$ | 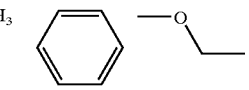 | —O— | 1 |  | — | 1 | 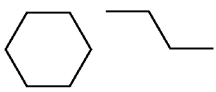 | —(CH$_2$)— | F | F |
| 123 | C$_3$H$_7$ | H |  | — | 1 |  | — | 1 |  | — | H | F |
| 124 | n-C$_4$H$_9$ | H |  | — | 1 |  | — | 1 |  | — | F | F |
| 125 | n-C$_5$H$_{11}$ | H |  | COO | 1 | 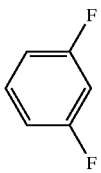 | — | 1 |  | — | H | F |
| 126 | CH$_3$ | H |  | — | 1 |  | — | 1 |  | — | F | Cl |
| 127 | C$_2$H$_5$ | H |  | — | 1 |  | — | 1 |  | —(CH$_2$)— | H | Cl |
| 128 | C$_3$H$_7$ | CH$_3$ | 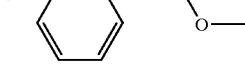 | —O— | 1 |  | — | 1 |  | — | F | Cl |
| 129 | n-C$_4$H$_9$ | H |  | — | 1 |  | — | 1 |  | — | H | Cl |
| 130 | n-C$_5$H$_{11}$ | H |  | — | 1 |  | — | 1 |  | — | F | Cl |
| 131 | CH$_3$ | H |  | — | 1 |  | — | 1 |  | — | H | Br |
| 132 | C$_2$H$_5$ | CH$_3$ | 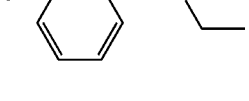 | —O— | 1 |  | — | 1 | 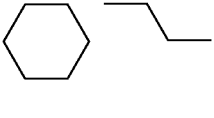 | —(CH$_2$)— | F | Br |

-continued

| No. | R | R' | A1 | Za | na | A2 | Zb | nc | A3 | Zc | Y | |
|---|---|---|---|---|---|---|---|---|---|---|---|---|
| 133 | $C_3H_7$ | H | phenyl | — | 1 | phenyl | — | 1 | 2-F-phenyl | — | H | Br |
| 134 | $n$-$C_4H_9$ | H | phenyl | — | 1 | 2-F-phenyl | — | 1 | phenyl | — | F | I |
| 135 | $n$-$C_5H_{11}$ | H | phenyl | — | 1 | 2,4-di-F-phenyl | — | 1 | cyclohexyl | — | H | I |
| 136 | $CH_3$ | H | phenyl | — | 1 | phenyl | — | 1 | phenyl | — | F | CN |
| 137 | $C_2H_5$ | H | phenyl | — | 1 | cyclohexyl | — | 1 | 2-F-phenyl-propyl | — | H | CN |
| 138 | $C_3H_7$ | $CH_3$ | phenyl | $-CH_2CH_2O-$ | 1 | phenyl | — | 1 | cyclohexyl | — | F | $-\equiv-CN$ |
| 139 | $n$-$C_4H_9$ | H | phenyl | — | 1 | phenyl | — | 1 | phenyl | — | H | $-\equiv-CN$ |
| 140 | $n$-$C_5H_{11}$ | H | phenyl | — | 1 | phenyl | — | 1 | phenyl | — | F | $-\equiv-CN$ |

Examples (use examples) of the liquid crystal composition containing the compound of the present invention is shown in the following, and the liquid crystal composition of the present invention is not limited to the examples.

Example 4

Use Example 1

The following liquid crystal composition (A1) was prepared from five liquid crystal compounds.

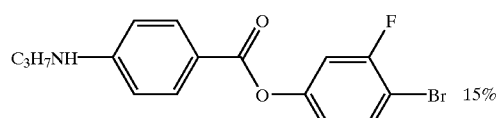

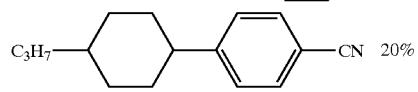

Physical properties of the liquid crystal composition (A1) were that NI was 65.0° C., Δε was 16.3, Δn was 0.1460, and η was 45.0 mPa·s. Threshold voltage using a liquid crystal cell having cell thickness of 9.1 μm was 1.20 V.

Example 5

Use Example 2

The following liquid crystal composition (A2) was prepared from five liquid crystal compounds.

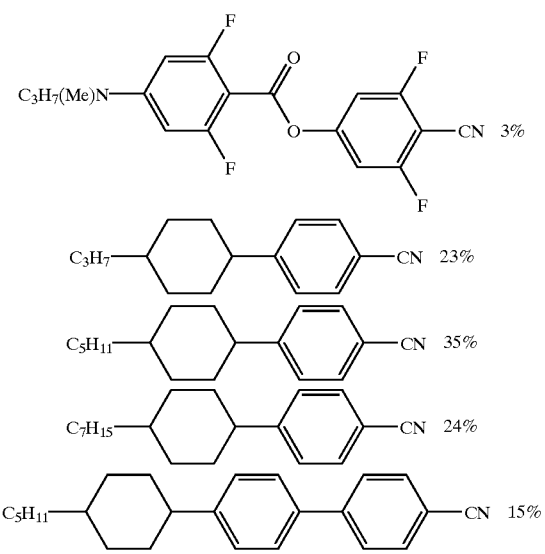

Physical properties of the liquid crystal composition (A2) were that NI was 67.8° C., Δε was 13.6, Δn was 0.138, and η was 29.4 mPa·s. The threshold voltage using a liquid crystal cell having cell thickness of 8.8 μm was 1.54 V.

Example 6

Comparative Example 1

By the use of 4-brom-3-fluorophenyl 4-buthylbenzoate which is known in the literature and has structure similar to that of the compound of the present invention, the liquid crystal composition (A12) which is similar to the liquid crystal composition (A1) was prepared

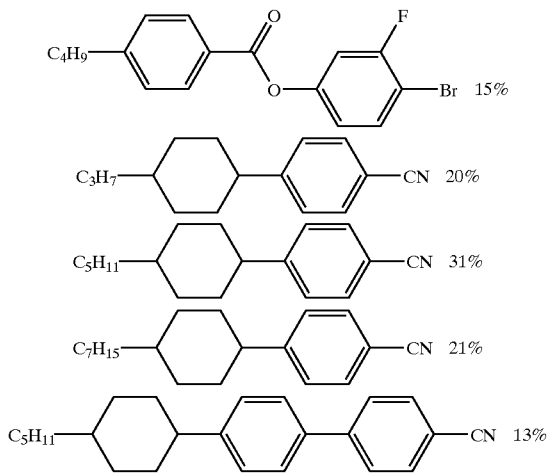

Physical properties of the liquid crystal composition (A12) were that NI was 58.8° C., Δε was 11.7, Δn was 0.1330, and η was 29.2 mPa·s. Threshold voltage using a liquid crystal cell having cell thickness of 9.2 μm was 1.47 V.

USE IN THE INDUSTRY

The compound of the present invention represented by general formula (1) has a wide temperature range of liquid crystal phase, low viscosity, and excellent miscibility with other liquid crystal compounds, and is a new liquid crystalline compound. New liquid crystal composition using the liquid crystal compound of the present invention has a wide temperature range of liquid crystal phase, a large value of dielectric anisotropy, a large value of optical anisotropy, and low threshold voltage compared with known and similar liquid crystal compounds. Then, driving voltage of the liquid crystal element can be reduced by the use of the liquid crystal composition.

As the compound of the present invention represented by general formula (1) has a large and positive value of optical anisotropy, steepness of the threshold voltage and a view angle in liquid crystal display element using the compound can be improved.

What is claimed is:

1. An aniline derivative represented by general formula (1)

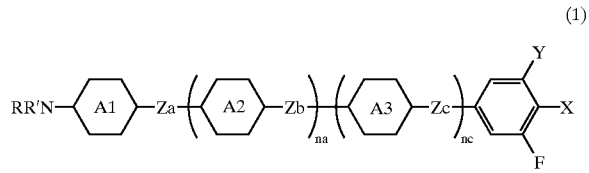

(1)

wherein R and R' represent independently of each other alkyl with 1 to 10 carbon, alkoxyalkyl with 1 to 10 carbon, or hydrogen; X represents cyano, halogen, haloalkyl, haloalkyloxy, or 2-cyanoethynyl; Y represents fluorine or hydrogen; na and nc represent independently of each other 0 or 1; Za, Zb, and Zc represent independently of each other a single bond, 1,2-ethylene, carbonyloxy, or oxymethylene; ring A1 represents 1,4-phenylene in which hydrogen may be replaced by fluorine; ring A2 and ring A3 represent independently of each other 1,4-cyclohexylene, 1,4-phenylene in which hydrogen may be replaced by fluorine, or 1,3-pyrimidine-2,5-diyl;

excluding the single aniline derivative where both of R and R' represent methyl, X represents chlorine, Y represents hydrogen, both of na and nc represent 0, Za represents a single bond, and ring A1 represents 1,4-phenylene.

2. The aniline derivative according to claim 1, wherein both of na and nc are 0.

3. The aniline derivative according to claim 1, wherein X is halogen, trihaloalkyl, or trihaloalkyloxy.

4. The aniline derivative according to claim 2, wherein X is cyano or 2-cyanoethynyl.

5. The aniline derivative according to claim 2, wherein Za is carbonyloxy.

6. The aniline derivative according to claim 5, wherein X is cyano or 2-cyanoethynyl.

7. The aniline derivative according to claim 1, wherein na is 1, and nc is 0.

8. The aniline derivative according to claim 7, wherein X is halogen.

9. The aniline derivative according to claim 7, wherein X is cyano or 2-cyanoethynyl.

10. The aniline derivative according to claim 7, wherein Zb is carbonyloxy.

11. The aniline derivative according to claim 9, wherein Zb is carbonyloxy.

12. The aniline derivative according to claim 1, wherein both of na and nc are 1.

13. A liquid crystal composition containing two or more components, at least of which is an aniline derivative according to any one of claims 1 to 12.

14. A liquid crystal composition comprising one or more compounds according to any one of claims 1 to 12 as the first component, and one or more compounds selected from the group consisting of general formulae (2), (3), and (4),

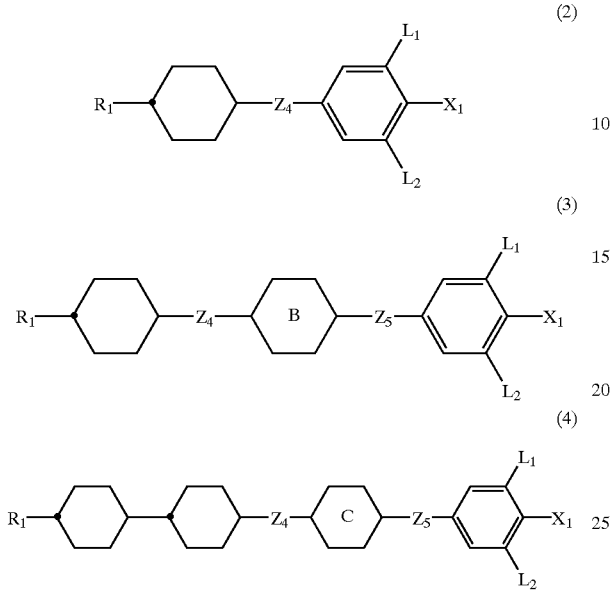

(2)

(3)

(4)

wherein $R_1$ represents alkyl having 1 to 10 carbon, any methylene nonadjacent each other in the alkyl may be replaced with oxygen or —CH=CH—, and any hydrogen in the alkyl may be replaced with fluorine, $X_1$ represents fluorine, chlorine, —OCF$_3$, —OCF$_2$H, —CF$_3$, —CF$_2$H, —CFH$_2$, —OCF$_2$CF$_2$H, or —OCF$_2$CFHCF$_3$; $L_1$ and $L_2$ independently of each other represent hydrogen or fluorine; $Z_4$ and $Z_5$ independently of each other 1,2-ethylene, 1,4-butylene, —COO—, —CF$_2$O—, —OCF$_2$—, —CH=CH—, or a single bond; ring B represents trans-1,4-cyclohexylene, 1,3-dioxane-2,5-diyl, or 1,4-phenylene in which hydrogen on the ring may be replaced by fluorine; ring C represents trans-1,4-cyclohexylene or 1,4-phenylene in which hydrogen on the ring may be replaced by fluorine.

15. A liquid crystal composition comprising one or more compounds according to any one of claims 1 to 12 as the first component and one or more compounds selected from the group consisting of formulae (5) and (6) as the second component,

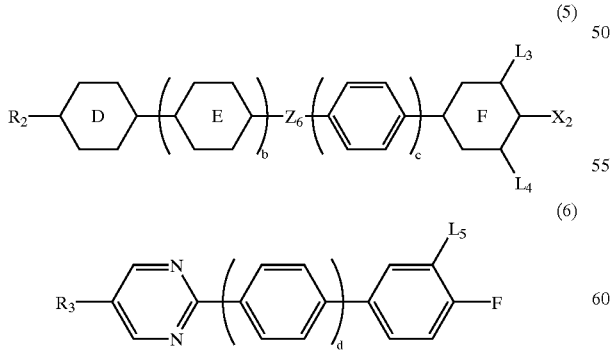

(5)

(6)

wherein $R_2$ and $R_3$ represent alkyl having 1 to 10 carbon and any methylene nonadjacent each other in the alkyl may be replaced with oxygen or —CH=CH—, and any hydrogen in the alkyl may be replaced with fluorine; $X_2$ represents —CN or —C≡C—CN ; ring D represents trans-1,4-cyclohexylene, 1,4-phenylene, or pyrimidine-2,5-diyl; ring F represents trans-1,4-cyclohexylene or 1,4-phenylene; $Z_6$ represent 1,2-ethylene, —COO— or a single bond; $L_3$, $L_4$, and $L_5$ represent independently of each other hydrogen or fluorine; b, c, and d represent independently of each other 0 or 1.

16. A liquid crystal composition comprising one or more compounds according to any one of claims 1 to 12 as the first component, one or more compounds selected from the group consisting of general formulae (2), (3), and (4) as the second component, and one or more compounds selected from the group consisting of general formulae (7), (8), and (9) as the third component,

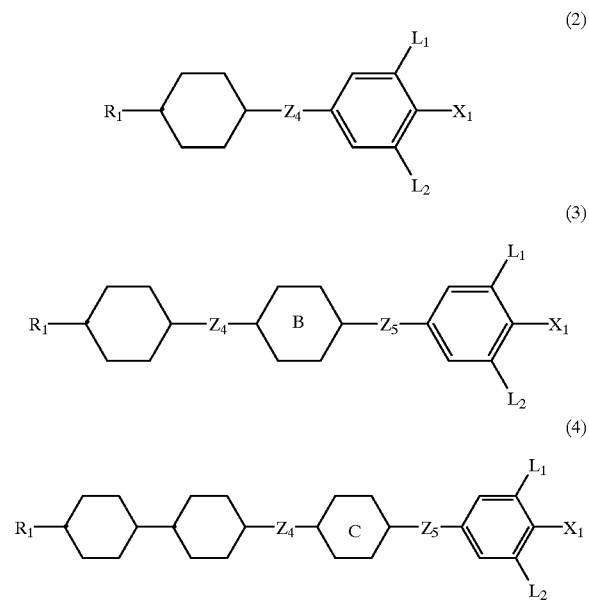

(2)

(3)

(4)

wherein $R_1$ represents alkyl having 1 to 10 carbon, any methylene nonadjacent each other in the alkyl may be replaced with oxygen or —CH=CH—; and any hydrogen in the alkyl may be replaced with fluorine; $X_1$ represents fluorine, chlorine, —OCF$_3$, —OCF$_2$H, —CF$_3$, —CF$_2$H, —CFH$_2$, —OCF$_2$CF$_2$H, or —OCF$_2$CFHCF$_3$; $L_1$ and $L_2$ independently of each other represent hydrogen or fluorine; $Z_4$ and $Z_5$ independently of each other 1,2-ethylene, 1,4-butylene, —COO—, —CF$_2$O—, —OCF$_2$—, —CH=CH—, or a single bond; ring B represents trans-1,4-cyclohexylene, 1,3-dioxane-2,5-diyl, or 1,4-phenylene in which hydrogen on the ring may be replaced by fluorine; ring C represents trans-1,4-cyclohexylene or 1,4-phenylene in which hydrogen on the ring may be replaced by fluorine,

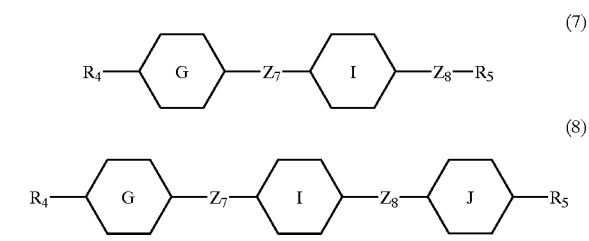

(7)

(8)

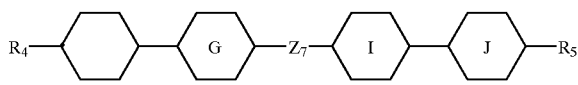
(9)

wherein $R_4$ and $R_5$ represent alkyl having 1 to 10 carbon, and any methylene nonadjacent each other in the alkyl may be replaced with oxygen or —CH=CH—, and any hydrogen in the alkyl may be replaced with fluorine; rings G, I, and J represent independently of each other trans-1,4-cyclohexylene, pyrimidine-2,5-diyl, or 1,4-phenylene in which hydrogen in the ring may be replaced with fluorine; $Z_7$ and $Z_8$ represent independently of each other —C≡C—, —COO—, —CH2CH2—, —CH=CH— or a single bond.

17. A liquid crystal composition comprising one or more compounds according to any one of claims 1 to 12 as the first component, one or more compounds selected from the group consisting of general formulae (5) and (6) as the second component, and one or more compounds selected from the group consisting of general formulae (7), (8), and (9) as the third component,

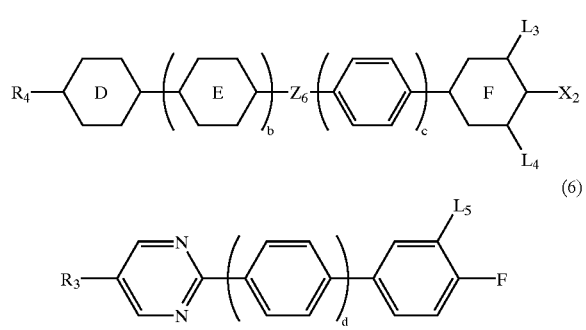

wherein $R_2$ and $R_3$ represent alkyl having 1 to 10 carbon and any methylene nonadjacent each other in the alkyl may be replaced with oxygen or —CH=CH—, and any hydrogen in the alkyl may be replaced with fluorine; $X_2$ represents —CN or —C≡C—CN ; ring D represents trans-1,4-cyclohexylene, 1,4-phenylene, or pyrimidine-2,5-diyl; ring F represents trans-1,4-cyclohexylene or 1,4-phenylene; $Z_6$ represent 1,2-ethylene,—COO— or a single bond; $L_3$, $L_4$, and $L_5$ represent independently of each other hydrogen or fluorine; b, c, and d represent independently of each other 0 or 1,

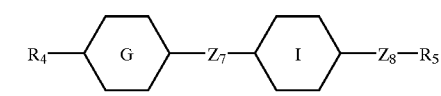
(7)

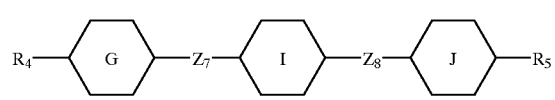
(8)

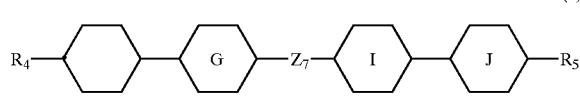
(9)

wherein $R_4$ and $R_5$ represent alkyl having 1 to 10 carbon, and any methylene nonadjacent each other in the alkyl may be replaced with oxygen or —CH=CH—, and any hydrogen in the alkyl may be replaced with fluorine; rings G, I, and J represent independently of each other trans-1,4-cyclohexylene, pyrimidine-2,5-diyl, or 1,4-phenylene in which hydrogen in the ring may be replaced with fluorine; $Z_7$ and $Z_8$ represent independently of each other —C≡C—, —COO—, —CH2CH2—, —CH=CH— or a single bond.

18. A liquid crystal composition comprising one or more compounds according to any one of claims 1 to 12 as the first component, one or more compounds selected from the group consisting of general formulae (2), (3), and (4) as the second component, and one or more compounds selected from the group consisting of formulae (5) and (6) as the third component,

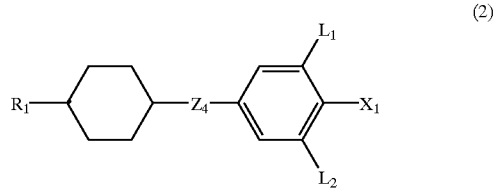
(2)

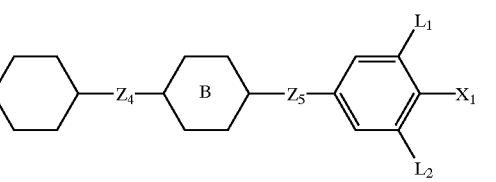
(3)

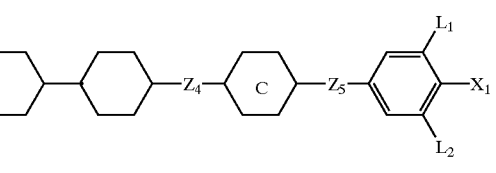
(4)

wherein $R_1$ represents alkyl having 1 to 10 carbon, any methylene nonadjacent each other in the alkyl may be replaced with oxygen or —CH=CH—, and any hydrogen in the alkyl may be replaced with fluorine; $X_1$ represents fluorine, chlorine, —OCF$_3$, —OCF$_2$H, —CF$_3$, —CF$_2$H, —CFH$_2$, —OCF$_2$CF$_2$H, or —OCF$_2$CFHCF$_3$; $L_1$ and $L_2$ independently of each other represent hydrogen or fluorine; $Z_4$ and $Z_5$ independently of each other 1,2-ethylene, 1,4-butylene, —COO—, —CF$_2$O—, —OCF$_2$—, —CH=CH—, or a single bond; ring B represents trans-1,4-cyclohexylene, 1,3-dioxane-2,5-diyl, or 1,4-phenylene in which hydrogen on the ring may be replaced by fluorine; ring C represents trans-1,4-cyclohexylene or 1,4-phenylene in which hydrogen on the ring may be replaced by fluorine,

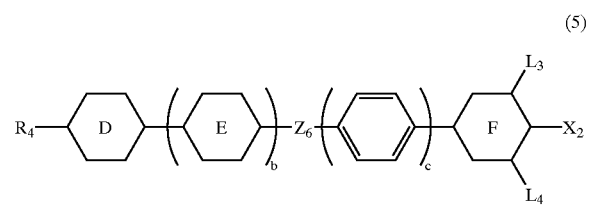
(5)

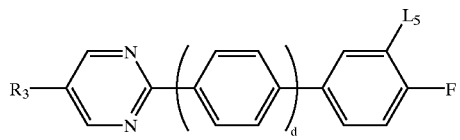 (6)

wherein R₂ and R₃ represent alkyl having 1 to 10 carbon and any methylene nonadjacent each other in the alkyl may be replaced with oxygen or —CH═CH—, and any hydrogen in the alkyl may be replaced with fluorine; X₂ represents —CN or —C≡C—CN ; ring D represents trans-1,4-cyclohexylene, 1,4-phenylene, or pyrimidine-2,5-diyl; ring F represents trans-1,4-cyclohexylene or 1,4-phenylene; $Z_6$ represent 1,2-ethylene, —COO— or a single bond; $L_3$, $L_4$, and $L_5$ represent independently of each other hydrogen or fluorine; b, c, and d represent independently of each other 0 or 1.

19. The liquid crystal composition according to claim 13, further comprising one or more optically active compounds.

20. A liquid crystal display element comprising the liquid crystal composition according to claim 13.

* * * * *

UNITED STATES PATENT AND TRADEMARK OFFICE
CERTIFICATE OF CORRECTION

PATENT NO.   : 6,485,799 B1
DATED        : November 26, 2002
INVENTOR(S)  : Atsuko Fujita et al.

It is certified that error appears in the above-identified patent and that said Letters Patent is hereby corrected as shown below:

Column 69, claim 17, change the first formula (formula (5)) to:

-- 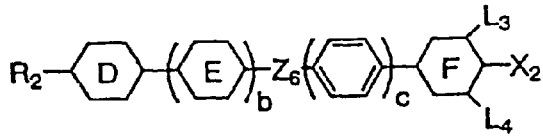 --.

Column 70, claim 18, change the fourth formula (formula (5)) to:

-- 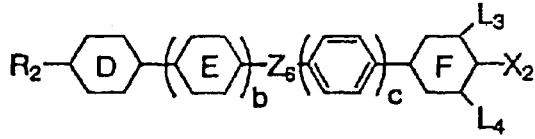 --.

Signed and Sealed this

Twenty-seventh Day of May, 2003

JAMES E. ROGAN
*Director of the United States Patent and Trademark Office*